(12) United States Patent  
Itoi

(10) Patent No.: US 10,084,140 B2  
(45) Date of Patent: Sep. 25, 2018

(54) MATERIAL FOR ORGANIC ELECTROLUMINESCENT DEVICE AND ORGANIC ELECTROLUMINESCENT DEVICE USING THE SAME

(71) Applicant: SAMSUNG DISPLAY CO., LTD., Yongin-si, Gyeonggi-do (KR)

(72) Inventor: Hiroaki Itoi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 388 days.

(21) Appl. No.: 14/856,415

(22) Filed: Sep. 16, 2015

(65) Prior Publication Data

US 2016/0118594 A1   Apr. 28, 2016

(30) Foreign Application Priority Data

Oct. 22, 2014   (JP) .................................. 2014-215597

(51) Int. Cl.
*H01L 51/50* (2006.01)
*H01L 51/00* (2006.01)
(Continued)

(52) U.S. Cl.
CPC ...... *H01L 51/0061* (2013.01); *C07D 491/048* (2013.01); *C07D 495/04* (2013.01);
(Continued)

(58) Field of Classification Search
None
See application file for complete search history.

(56) References Cited

U.S. PATENT DOCUMENTS

2013/0060037 A1   3/2013 Lin et al.

FOREIGN PATENT DOCUMENTS

| JP | 2008-074939 | * | 4/2008 | ............. H01L 51/50 |
| JP | 2009-29726 A | | 2/2009 | |

(Continued)

*Primary Examiner* — Gregory D Clark
(74) *Attorney, Agent, or Firm* — Lewis Roca Rothgerber Christie LLP

(57) ABSTRACT

Provided are a material for an organic electroluminescent device and an organic electroluminescent device including the same. The material for the organic electroluminescent device is represented by the following Formula (1). The material and the organic electroluminescent device including the material may have long life. The material may include an azadibenzoheterole part at the meta (m) position of a phenylene group combined via a direct linkage or a connecting group $L_1$ with the nitrogen atom N of an amine.

Formula 1

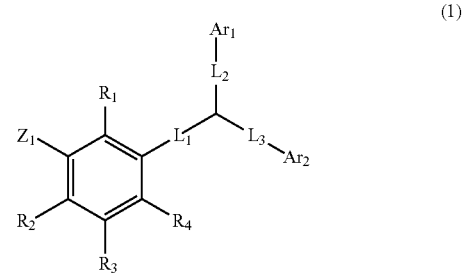

4 Claims, 1 Drawing Sheet

(51) Int. Cl.
*C07D 491/048* (2006.01)
*C07D 495/04* (2006.01)
*H01L 51/52* (2006.01)

(52) U.S. Cl.
CPC ...... *H01L 51/0071* (2013.01); *H01L 51/0094* (2013.01); *H01L 51/5012* (2013.01); *H01L 51/5056* (2013.01); *H01L 51/5206* (2013.01)

(56) References Cited

FOREIGN PATENT DOCUMENTS

| | | |
|---|---|---|
| JP | 2009-267255 A | 11/2009 |
| JP | 2012-515216 A | 7/2012 |
| JP | 2013-28605 A | 2/2013 |
| JP | 2014-43444 A | 3/2014 |
| WO | WO 2012/090967 A1 | 7/2012 |
| WO | WO 2013/180020 A1 | 12/2013 |
| WO | WO 2014/065073 A1 | 5/2014 |

* cited by examiner

MATERIAL FOR ORGANIC ELECTROLUMINESCENT DEVICE AND ORGANIC ELECTROLUMINESCENT DEVICE USING THE SAME

CROSS-REFERENCE TO RELATED APPLICATION

This application claims priority to and the benefit of Japanese Patent Application No. 2014-215597, filed on Oct. 22, 2014, the entire content of which is incorporated herein by reference.

BACKGROUND

Recently, an organic electroluminescent display (organic EL display) is being actively developed as an image display apparatus. The organic EL display is, unlike a liquid crystal display or the like, a so-called self luminescent type (or kind of) display which embodies display through light emission of a luminescent material including an organic compound in an emission layer by recombining holes and electrons injected from an anode and a cathode in the emission layer.

An example of an organic electroluminescent device (organic EL device) includes an anode, a hole transport layer disposed on the anode, an emission layer disposed on the hole transport layer, an electron transport layer disposed on the emission layer and a cathode disposed on the electron transport layer. Holes are injected from the anode, and the injected holes are injected via the hole transport layer into the emission layer. Meanwhile, electrons are injected from the cathode, and the injected electrons are injected via the electron transport layer into the emission layer. The holes and the electrons injected into the emission layer are recombined (or combined), and excitons are generated in the emission layer. The organic EL device emits light using light generated by the radiation deactivation of the excitons. The organic EL device is not limited to the aforementioned configuration, but many modifications thereof are possible.

For the application of an organic EL device in a display, the organic EL device should have high efficiency and long life. For example, in a blue emission region, the driving voltage of the organic EL device is high and the emission efficiency thereof is undesirable or insufficient when compared to a green emission region and a red emission region. To realize the high efficiency and the long life of the organic EL device, the normalization, the stabilization and the increase of the durability of a hole transport layer are examined.

As a hole transport material used in a hole transport layer, various suitable compounds such as an aromatic amine compound have been used, however tasks concerning the life of a device remain. As favorable materials for the increase of the life of the organic EL device, an amine derivative substituted with, for example, an aryl group or a heteroaryl group was suggested. However, an organic EL device using the above-mentioned materials has undesirable or insufficient emission life. Thus, studies on an organic EL device having increased emission life are continuously required.

SUMMARY

The present disclosure provides for solving the above-described tasks, a material for an organic EL device having long life and an organic EL device using the same.

The present disclosure herein relates to a material for an organic electroluminescent device and an organic electroluminescent device using the same. For example, embodiments of the present disclosure relate to a hole transport material for an organic electroluminescent device having long life and an organic electroluminescent device using the same.

For example, the present disclosure provides a material for an organic EL device having long life and used in at least one layer of stacking layers disposed between an emission layer and an anode and an organic EL device using the same.

Embodiments of the present disclosure provide materials for an organic EL device represented by the following Formula (1).

Formula 1

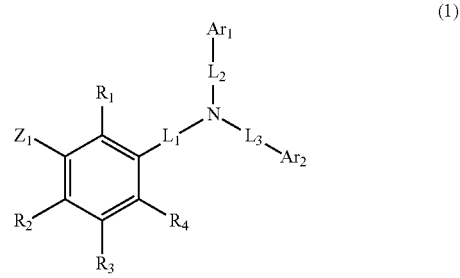

(1)

Where $R_1$ to $R_4$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom, $L_1$ to $L_3$ are each independently a direct linkage (e.g., a bond, such as a single bond) or a divalent group selected from the group consisting of a substituted or unsubstituted alkylene group, aralkylene group, arylene group, heteroarylene group and silyl group, $Ar_1$ and $Ar_2$ are each independently a substituted or unsubstituted aryl group having 6 to 30 carbon atoms for forming a ring or a substituted or unsubstituted heteroaryl group having 1 to 30 carbon atoms for forming a ring, and $Z_1$ is a monovalent group represented by the following Formula (2).

Formula 2

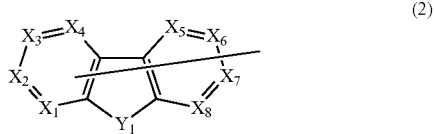

(2)

Where $X_1$ to $X_5$ are each independently N or $CR_5$, and at least one thereof is N, $Y_1$ is O, S, $CR_6R_7$ or $SiR_8R_9$, $R_5$ to $R_9$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom.

Since the material for an organic EL device of embodiments of the present disclosure introduces (includes) an azadibenzoheterole part (an azadibenzoheterole group) at the meta (m) part (meta position) of a phenylene group combining with an amine directly or via $L_1$, the amorphous properties of the material may be improved and the mobility of charge may be increased. In addition, since the azadibenzoheterole part (the azadibenzoheterole group) has electron accepting properties, electron tolerance may be improved and the increase of the life of the material may be attained. Thus, the long life of the organic EL device may be realized. For example, remarkable effects may be obtained in a blue emission region.

In other embodiments of the present disclosure, materials for an organic EL device represented by the following Formula (3) are provided.

Formula 3

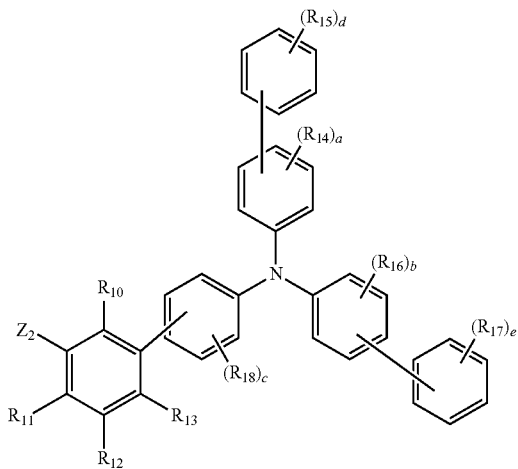

(3)

where $R_{10}$ to $R_{18}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom, a to c are each independently an integer from 0 to 4, d and e are each independently an integer from 0 to 5, and $Z_2$ is a monovalent group represented by the following Formula (4).

Formula 4

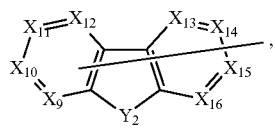

(4)

where $X_9$ to $X_{16}$ are each independently N or $CR_{19}$, and at least one thereof is N, $Y_2$ is O, S, $CR_{20}R_{21}$ or $SiR_{22}R_{23}$, $R_{19}$ to $R_{23}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom.

In the material for an organic EL device according to an embodiment of the present disclosure, each of $Ar_1$, $Ar_2$, and $L_1$ to $L_3$ is a substituted or unsubstituted phenyl group or phenylene group, and the conjugation of amine may be secured, and the charge tolerance of the material may be improved.

In still other embodiments of the present disclosure, organic EL devices including one of the above materials for an organic EL device in at least one layer of stacking layers disposed between an emission layer and an anode are provided.

The organic EL device according to an embodiment of the present disclosure uses one of the above materials for an organic EL device in at least one layer of stacking layers disposed between the emission layer and the anode, and long life thereof may be realized. For example, remarkable effects may be obtained in a blue emission region.

According to embodiments of the present disclosure, a material for an organic EL device realizing long life and an organic EL device using the same may be provided. For example, according to embodiments of the present disclosure, in a blue emission region, a material for an organic EL device used in at least one layer of stacking layers disposed between an emission layer and an anode and realizing long life, and an organic EL device using the same may be provided. The material for an organic EL device of embodiments of the present disclosure introduces (includes) an azadibenzoheterole part (an azadibenzoheterole group) at the meta (m) position of a phenylene group combined via a direct linkage (e.g., a bond, such as a single bond) or a connecting group $L_1$ with the nitrogen atom N of an amine, and the amorphous properties of the material for an organic EL device may be improved, charge mobility may be increased, and the electron tolerance of the material may be improved due to the electron accepting azadibenzoheterole part (azadibenzoheterole group). Thus, the long life of the organic EL device may be realized.

BRIEF DESCRIPTION OF THE DRAWINGS

The accompanying drawings are included to provide a further understanding of embodiments of the present disclosure, and are incorporated in and constitute a part of this specification. The drawings illustrate example embodiments of the present disclosure and, together with the description, serve to explain principles of embodiments of the present disclosure. In the drawings.

DETAILED DESCRIPTION

Figure 1:
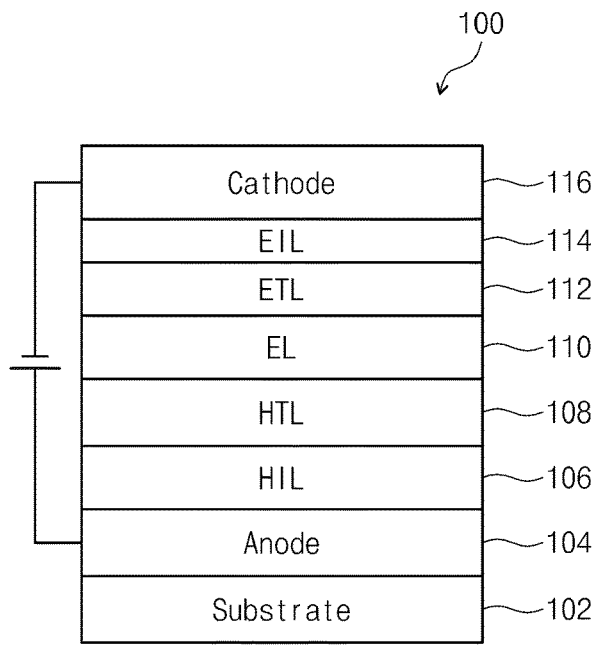
FIG. 1 is a schematic diagram illustrating an organic EL device 100 according to an embodiment of the present disclosure.

Embodiments of the present disclosure solve the above-described defects and provide long life by way of an azadibenzoheterole part (an azadibenzoheterole group) at the meta (m) position of a phenylene group combined via a direct linkage (e.g., a bond, such as a single bond) or a connecting group $L_1$ with the nitrogen atom (N) of an amine, and thereby the amorphous properties of the material for an organic EL device might be improved, charge mobility might be increased, and the electron tolerance of a material might be improved due to the electron accepting azadibenzoheterole part (azadibenzoheterole group), thereby realizing long life.

Hereinafter, the material for an organic EL device and the organic EL device using the same according to embodiments of the present disclosure will be described with reference to the accompanying drawings. The material for an organic EL device and the organic EL device using the same according to embodiments of the present disclosure may, however, be embodied in different forms and should not be construed as being limited to the embodiments set forth herein. In the drawings, like reference numerals refer to like elements or elements having like functions throughout, and repeated explanation thereof is not necessary.

The material for an organic EL device according to embodiments of the present disclosure is an amine compound introducing (including) an azadibenzoheterole part (an azadibenzoheterole group) at the meta (m) position of a phenylene group combined with an amine and is represented by the following Formula (1).

Formula 1

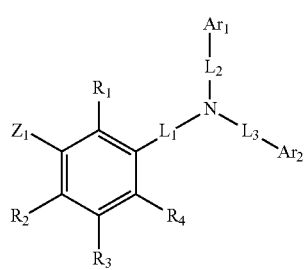

(1)

In the material for an organic EL device according to embodiments of the present disclosure and in Formula (1), $R_1$ to $R_4$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom, and $L_1$ to $L_3$ are each independently a direct linkage (e.g., a bond, such as a single bond) or a divalent group selected from the group consisting of a substituted or unsubstituted alkylene group, aralkylene group, arylene group, heteroarylene group and silyl group. As used herein, the statement "atoms for forming a ring" refers to ring forming atoms that may be the part of a same ring of different rings. $Ar_1$ and $Ar_2$ are each independently a substituted or unsubstituted aryl group having 6 to 30 carbon atoms for forming a ring or a substituted or unsubstituted heteroaryl group having 1 to 30 carbon atoms for forming a ring, and $Z_1$ is a monovalent group represented by the following Formula (2).

Formula 2

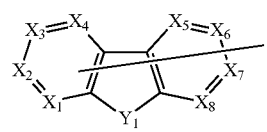

(2)

In Formula (2), $X_1$ to $X_8$ are each independently N or $CR_5$, and at least one thereof (e.g., at least one of $X_1$ to $X_8$) is N, and $Y_1$ is O, S, $CR_6R_7$ or $SiR_8R_9$. $R_5$ to $R_9$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom. In $X_1$ to $X_8$, the number of the nitrogen atom (N) may preferably be one; however the present disclosure is not limited thereto.

Here, the substituted or unsubstituted aryl group having 6 to 30 carbon atoms for forming a ring used in $R_1$ to $R_9$ in Formulae (1) and (2) may include a phenyl group, a naphthyl group, an anthracenyl group, a phenanthryl group, a biphenyl group, a terphenyl group, a quaterphenyl group, a quinqphenyl group, a sexiphenyl group, a fluorenyl group, a triphenylene group, a biphenylene group, a pyrenyl group, a benzofluoranthenyl group, a glyceryl group, and/or the like, without limitation.

In addition, the substituted or unsubstituted heteroaryl group having 1 to 30 carbon atoms for forming a ring used in $R_1$ to $R_9$ may include a pyridyl group, a furyl group, a thienyl group, a quinolyl group, an isoquinolyl group, a benzofuryl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, and/or the like, without limitation.

The alkyl group having 1 to 15 carbon atoms used in $R_1$ to $R_9$ may include a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, and/or the like.

In addition, the silyl group used in $R_1$ to $R_9$ may include a trialkylsilyl group, a triarylsilyl group, a monoalkyldiarylsilyl group, a dialkylmonoarylsilyl group, and/or the like, such as a trimethylsilyl group, a triphenylsilyl group, and/or the like.

In addition, the halogen atom used in $R_1$ to $R_9$ may include a fluorine atom (F), a chlorine atom (Cl), a bromine atom (Br), and/or the like.

In addition, $R_1$ to $R_9$ may be a hydrogen atom or a deuterium atom

In Formulae (1) and (2), a plurality (e.g., two or more) of adjacent $R_1$ to $R_9$ may be combined to each other to form a saturated or unsaturated ring.

In Formula (1), the substituted or unsubstituted aryl group having 6 to 30 carbon atoms for forming a ring used in $Ar_1$ and $Ar_2$ may include a phenyl group, a naphthyl group, an anthracenyl group, a phenanthryl group, a biphenyl group, a terphenyl group, a quaterphenyl group, a fluorenyl group, a triphenylene group, a biphenylene group, a pyrenyl group, a benzofluoranthenyl group, a glyceryl group, a phenylnaphthyl group, a naphthylphenyl group, and/or the like, without limitation. As $Ar_1$ and $Ar_2$, the substituted or unsubstituted phenylene group may be preferably used.

In addition, the substituted or unsubstituted heteroaryl group having 1 to 30 carbon atoms for forming a ring used in $Ar_1$ and $Ar_2$ may include a pyridyl group, a furyl group, a thienyl group, a quinolyl group, an isoquinolyl group, a benzofuryl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, and/or the like, without limitation.

In Formula (1), the substituted or unsubstituted alkylene group used in $L_1$ to $L_3$ as the divalent connecting group, a methylene group, an ethylene group, an n-propylene group, an n-butylene group, an n-hexylene group, an n-heptylene group, an n-octylene group, an n-dodecylene group, and/or the like, may be used without limitation.

In addition, the substituted or unsubstituted aralkylene group used in $L_1$ to $L_3$ as the divalent connecting group may be represented by $-(CH_2)_x-Ar'-$, $-Ar'-(CH_2)_x-$, or $-(CH_2)_x-Ar'-(CH_2)_y-$. Ar' represents an arylene group having 6 to 18 carbon atoms for forming a ring such as a phenylene group, a naphthylene group, and/or the like, and each of x and y represents an integer from 1 to 24. The sum of the carbon numbers of the arylene group represented by x, y and Ar' may be from 7 to 20, and may preferably be from 7 to 14, without limitation.

In addition, the substituted or unsubstituted arylene group used in $L_1$ to $L_3$ as the divalent connecting group may include a phenylene group, a biphenylene group, a terphenylene group, a naphthylene group, an anthracenylene group, a fluorenylene group, a triphenylene group, and/or the like, without limitation. As $L_1$ to $L_3$, the substituted or unsubstituted phenylene group may be preferably used.

In addition, the substituted or unsubstituted heteroarylene group used in $L_1$ to $L_3$ as the divalent connecting group may include a pyridylene group, a dibenzofurylene group, a dibenzoethylylene group, and/or the like, without limitation.

In addition, the substituted or unsubstituted silyl group used in $L_1$ to $L_3$ as the divalent connecting group may include a dimethylsilylene group and/or a diphenylsilylene group.

As described above, the amorphous properties of the material for an organic EL device may be improved and the mobility of charge may be increased by introducing an azadibenzoheterole part (an azadibenzoheterole group) at the meta (m) position of a phenylene group combined to the nitrogen atom (N) of an amine directly (e.g., by a bond, such as a single bond) or via $L_1$ in the material for an organic EL device according to embodiments of the present disclosure. Thus, the properties of the amine of increasing the life (e.g., the life of the organic EL device) may be maintained. In addition, by introducing (including) the azadibenzoheterole part (the azadibenzoheterole group) with high electron accepting properties, the electron tolerance of the material for an organic EL device may be increased, the durability of the material may be improved, and the life of the organic EL device may be increased further.

In addition, in the material for an organic EL device according to embodiments of Formula (1), $Ar_1$ and $Ar_2$ may preferably be each independently a substituted or unsubstituted phenyl group, and $L_1$ to $L_3$ are each independently a substituted or unsubstituted phenylene group. For example, the material for an organic EL device according to embodiments of the present disclosure may preferably be an amine compound represented by the following Formula (3).

Formula 3

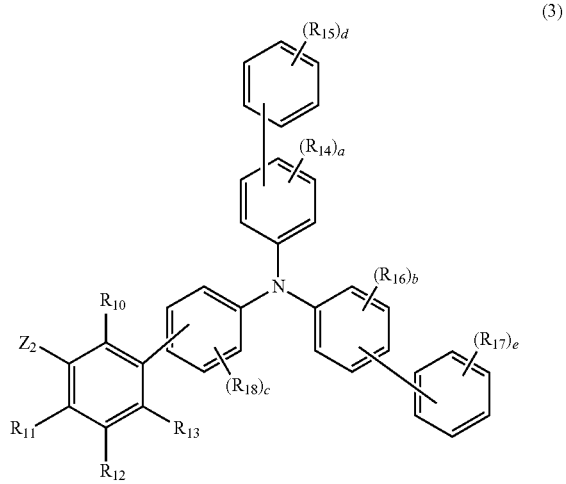

(3)

where $R_{10}$ to $R_{18}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom, a to c are each independently an integer from 0 to 4, d and e are each independently an integer from 0 to 5, and $Z_2$ is a monovalent group represented by the following Formula (4).

Formula 4

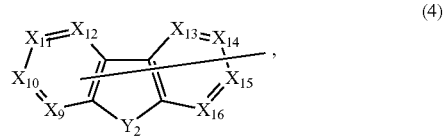

(4)

where $X_9$ to $X_{16}$ are each independently N or $CR_{19}$, and at least one thereof (e.g., at least one of $X_9$ to $X_{16}$) is N, and $Y_2$ is O, S, $CR_{20}R_{21}$ or $SiR_{22}R_{23}$. $R_{19}$ to $R_{23}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom. In $X_9$ to $X_{16}$, the number of nitrogen atoms (N) included in $X_9$ to $X_{16}$ may preferably be one, without limitation.

In Formulae (3) and (4), the substituted or unsubstituted aryl group having 6 to 30 carbon atoms for forming a ring, the substituted or unsubstituted heteroaryl group having 1 to 30 carbon atoms for forming a ring, the alkyl group having 1 to 15 carbon atoms, the silyl group and the halogen atom used in $R_{10}$ to $R_{23}$ may be the same as the substituted or unsubstituted aryl group having 6 to 30 carbon atoms for forming a ring, the substituted or unsubstituted heteroaryl group having 1 to 30 carbon atoms for forming a ring, the alkyl group having 1 to 15 carbon atoms, the substituted or unsubstituted silyl group and the halogen atom used in $R_1$ to $R_9$ In Formula (1).

In Formulae (3) and (4), a plurality (e.g., two or more) of adjacent $R_{10}$ to $R_{23}$ may be combined to each other to form a saturated or unsaturated ring.

In Formula (1) of the material for an organic EL device according to embodiments of the present disclosure, $Ar_1$ and $Ar_2$ are each independently a substituted or unsubstituted phenyl group, and $L_1$ to $L_3$ are each independently a substituted or unsubstituted phenylene group. Thus, the conjugation of an amine may be secured, and the charge tolerance of the material may be improved.

Examples of the material for an organic EL device according to embodiments of the present disclosure may include one material of the following Compounds 1 to 84.

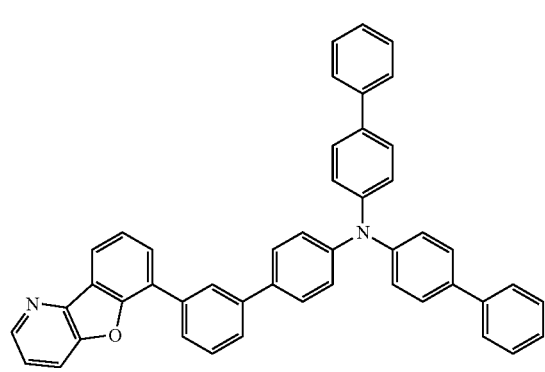

1

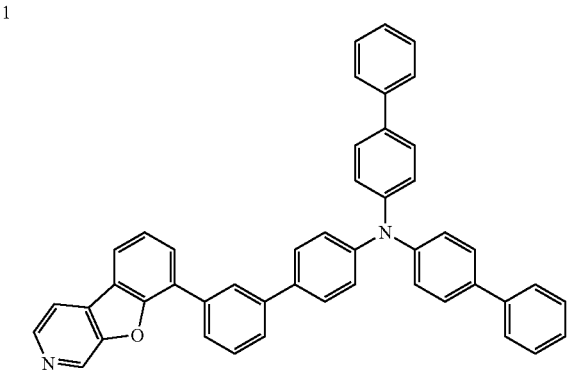

2

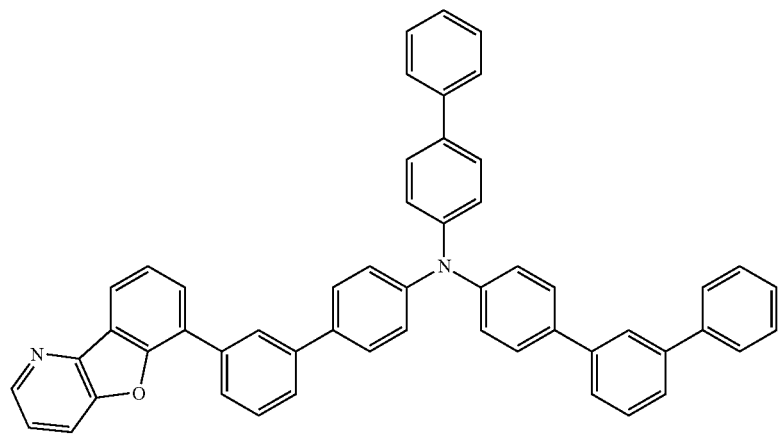

3

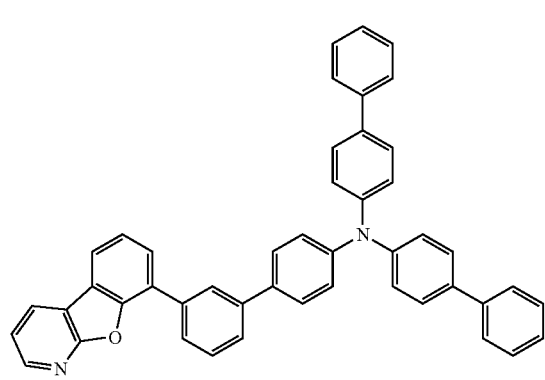

4

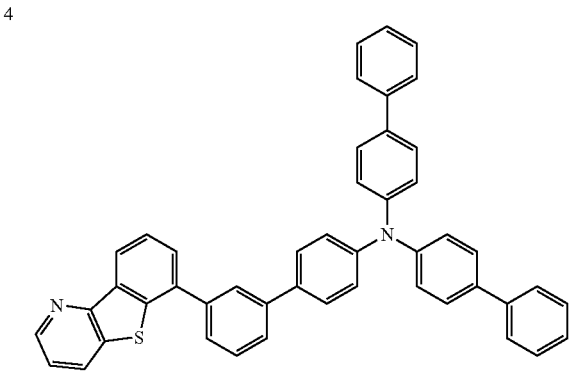

5

-continued
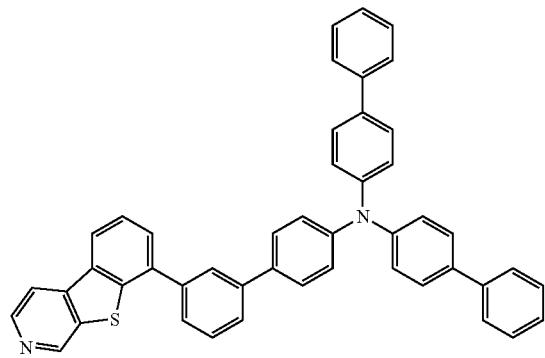
6
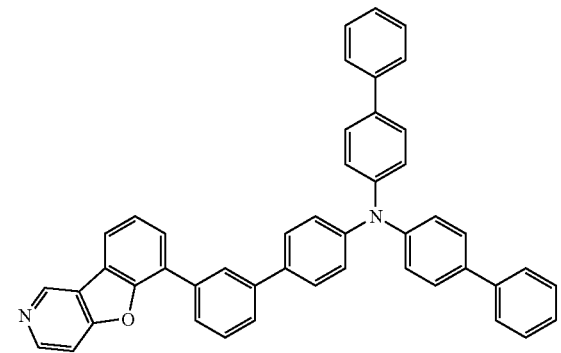
7
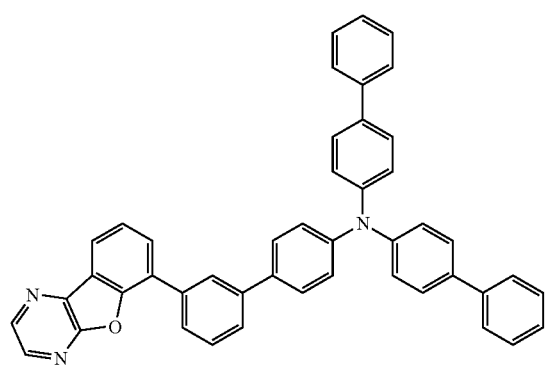
8
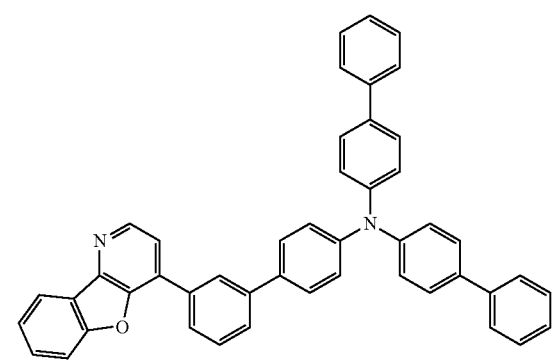
9
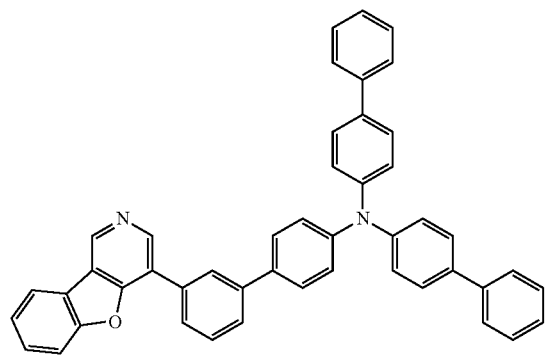
10
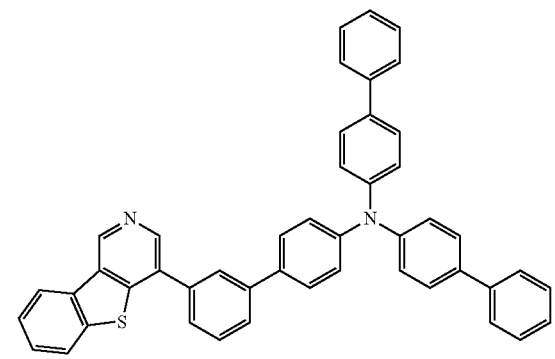
11
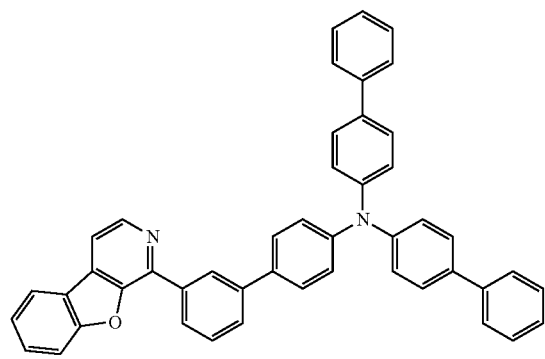
12

-continued
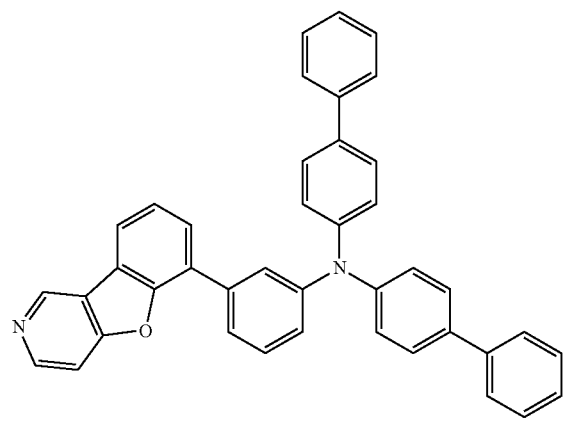
13
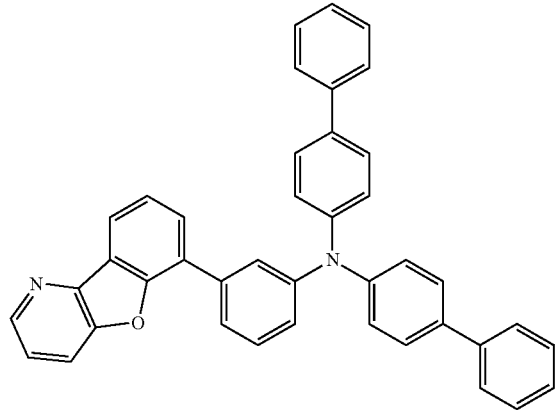
14
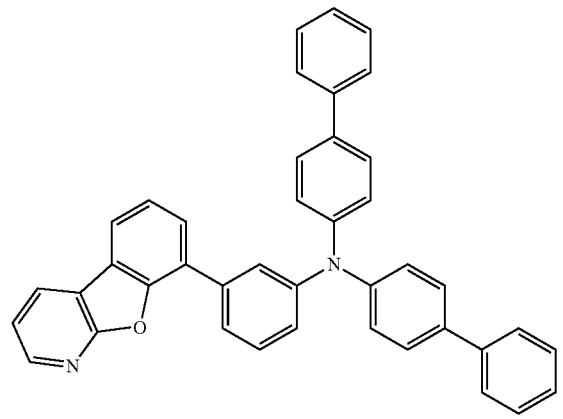
15
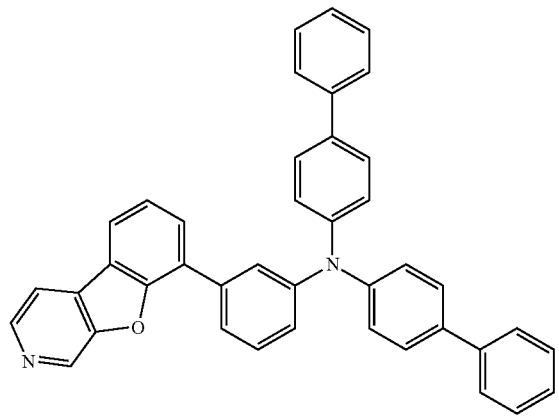
16
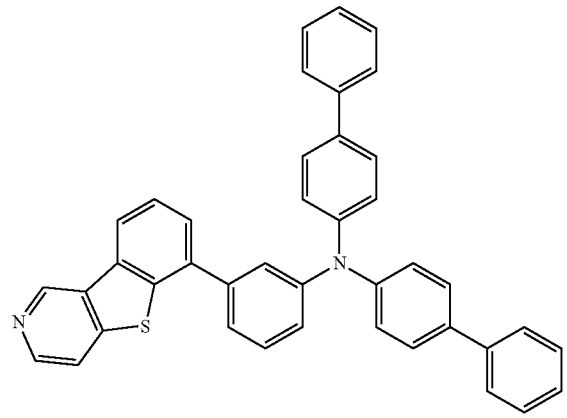
17
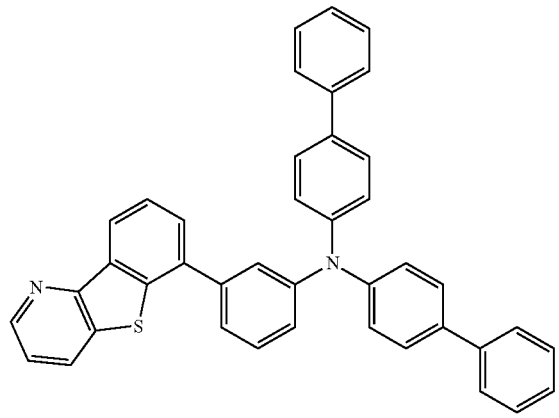
18

-continued
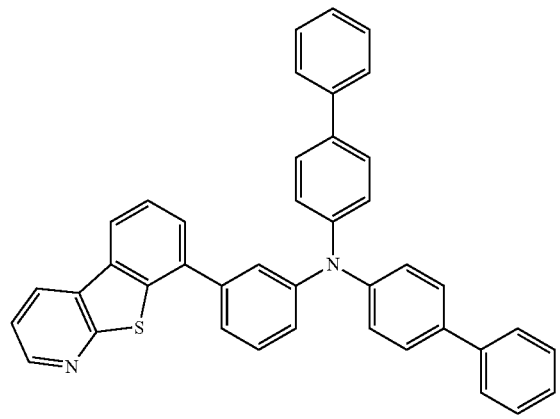
19
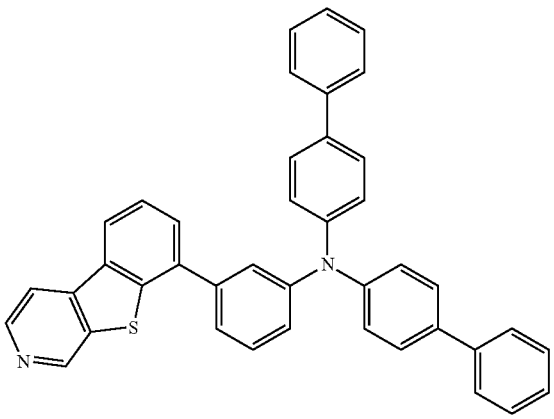
20
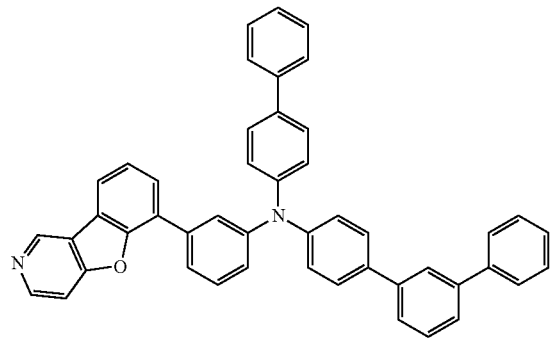
21
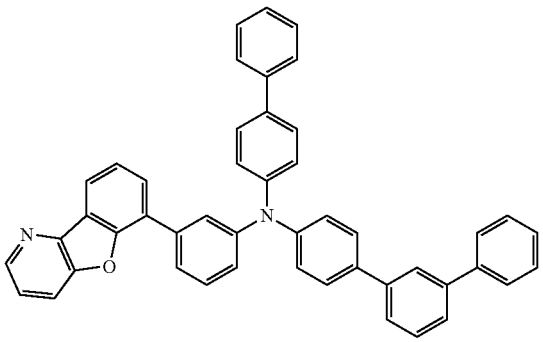
22
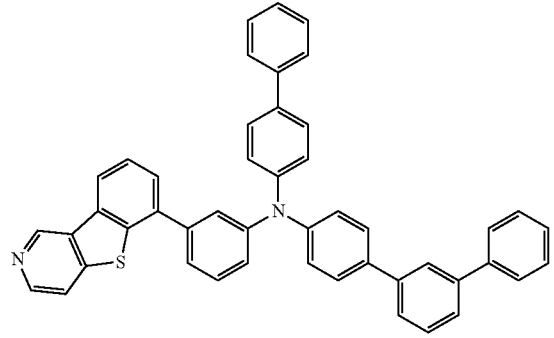
23
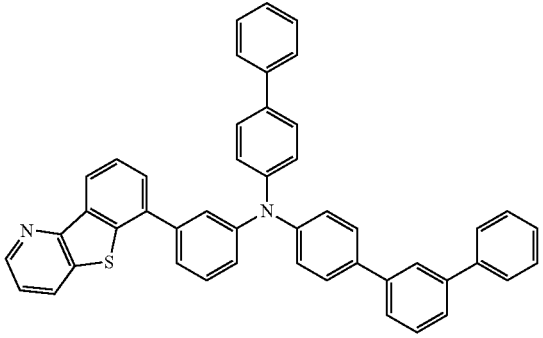
24
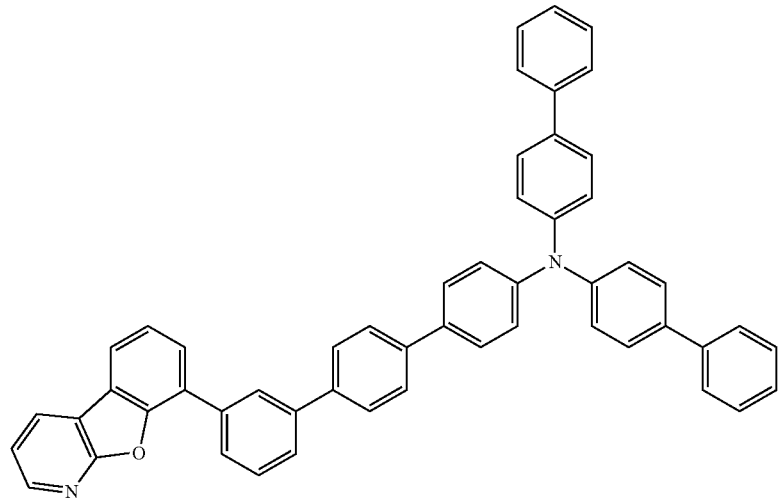
25

26
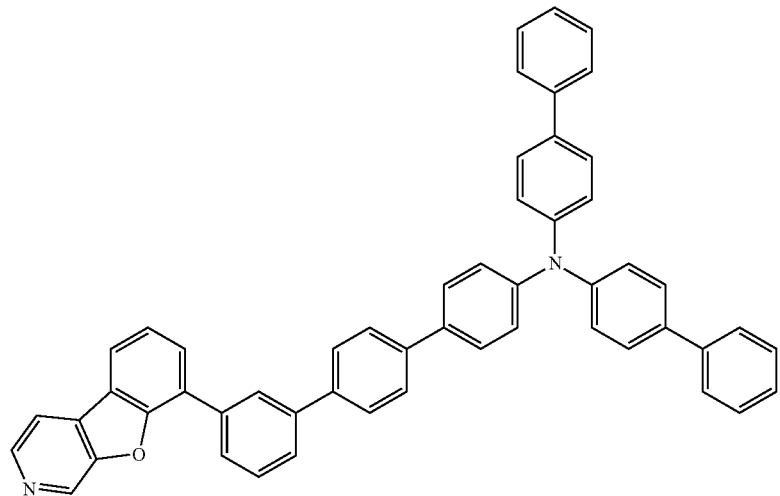
27
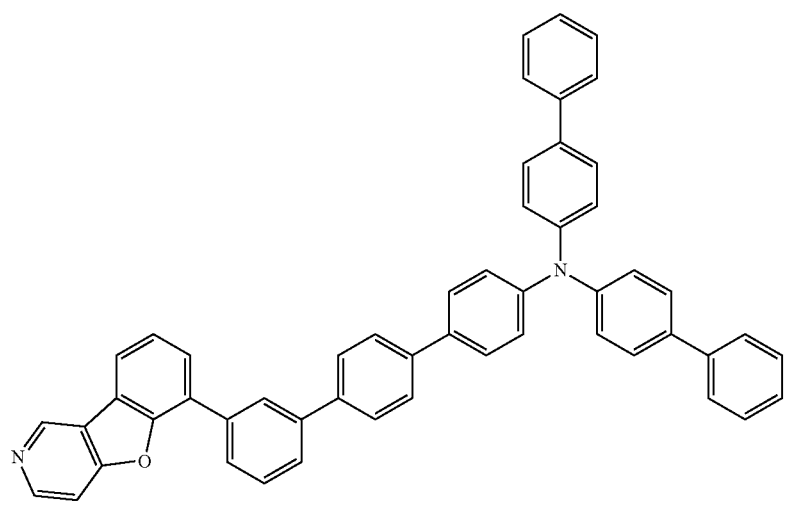
28
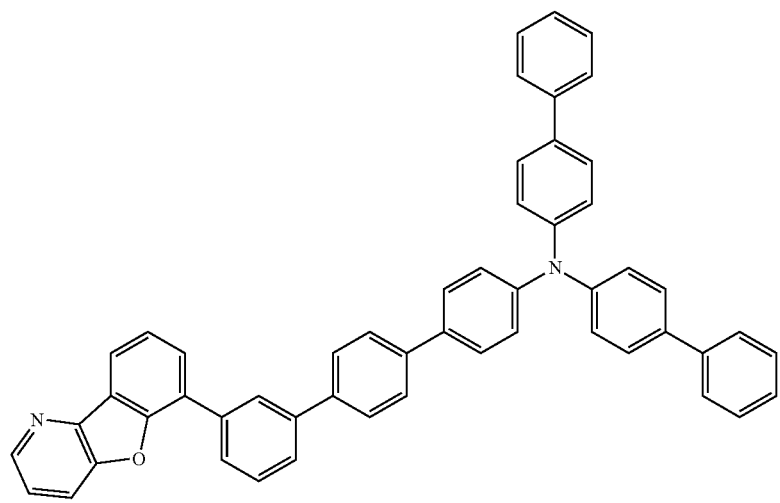

-continued
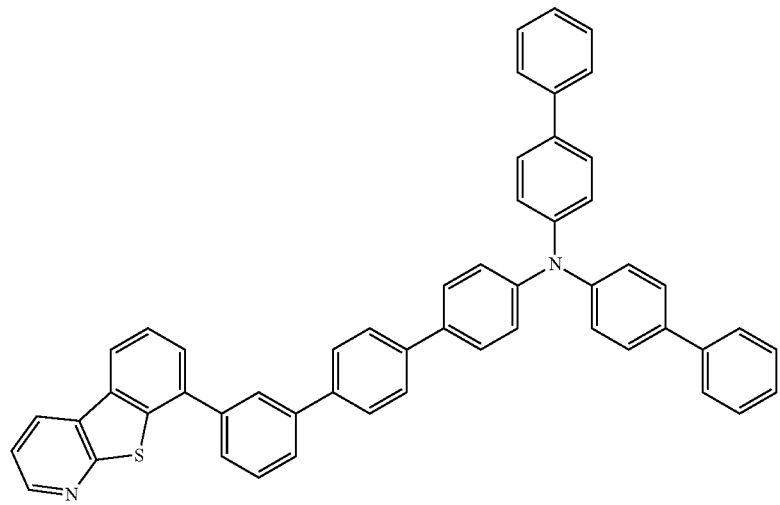
29
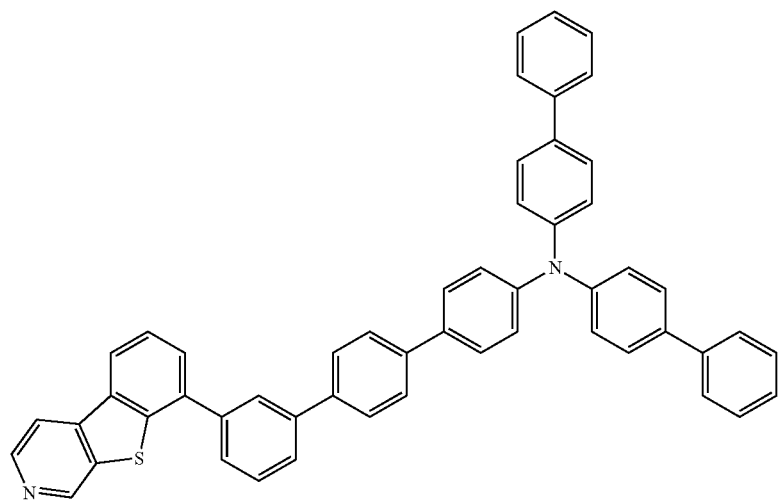
30
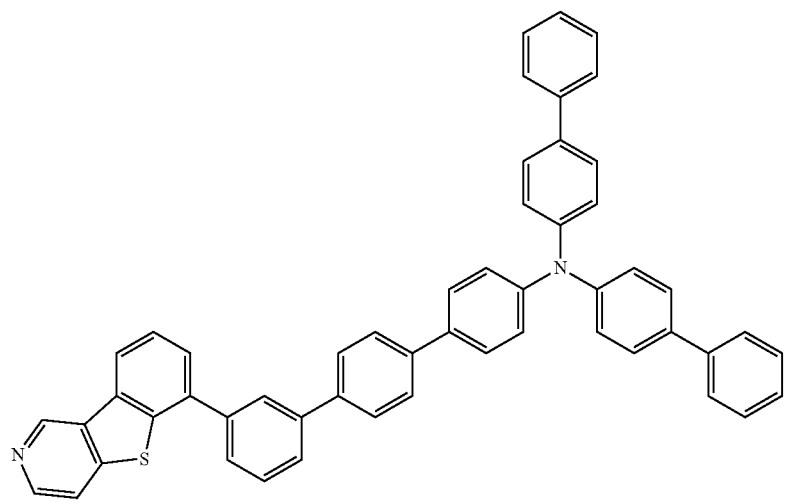
31

-continued
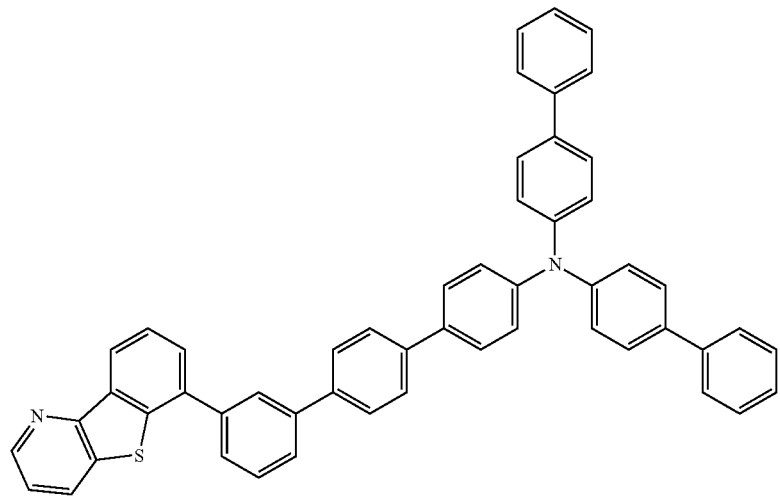
32
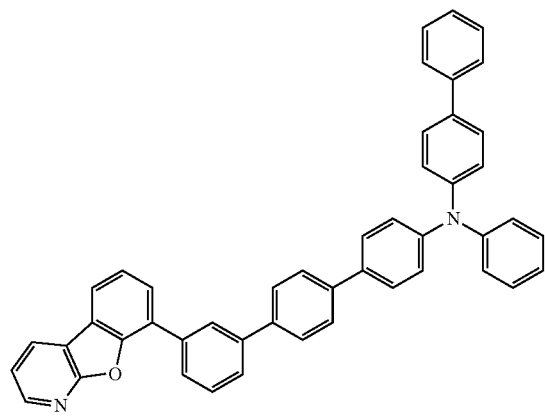
33
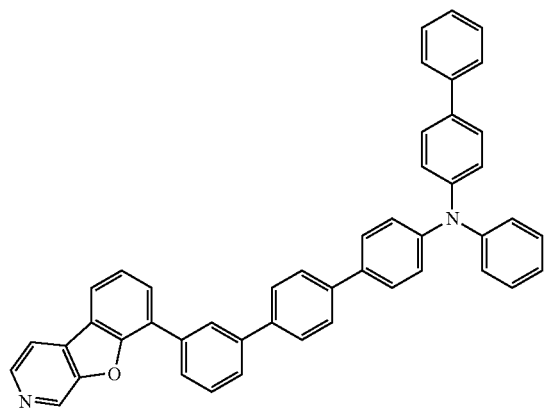
34
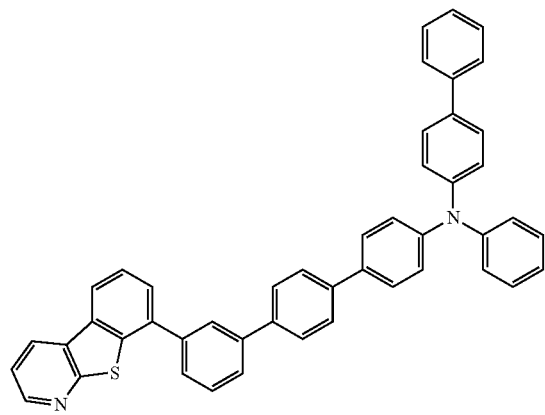
35
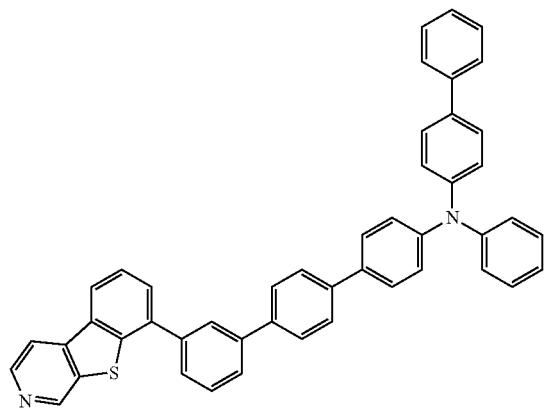
36

-continued
37
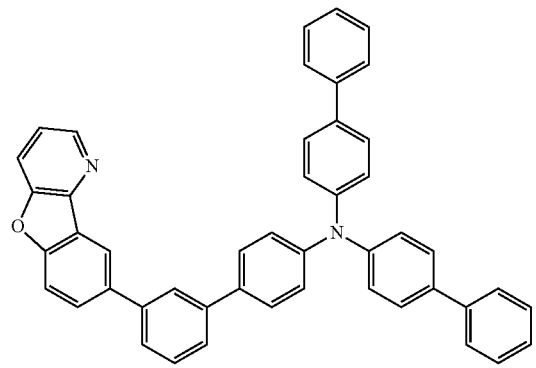
38
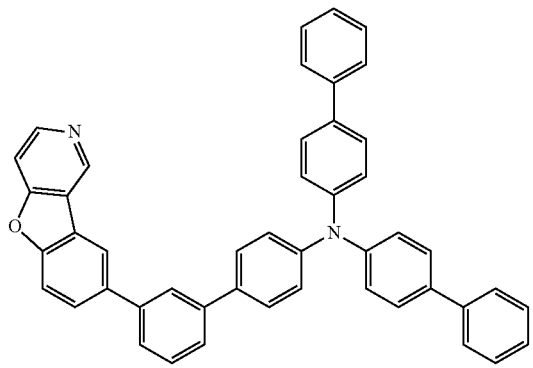
39
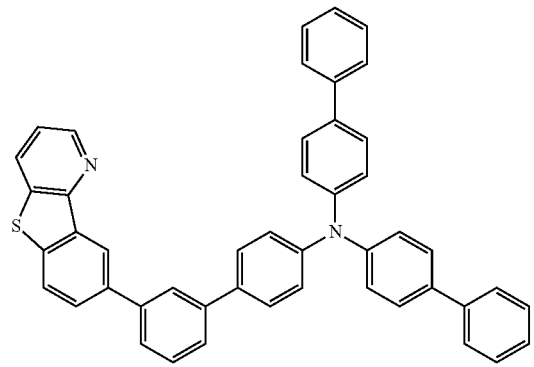
40
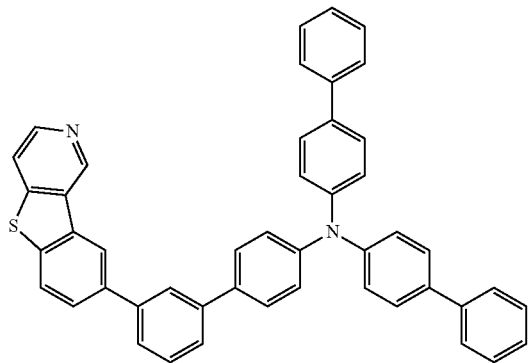
41
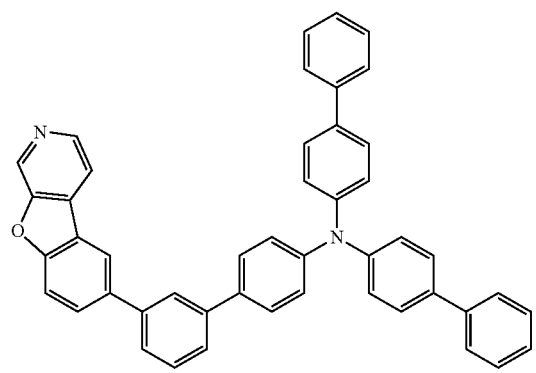
42
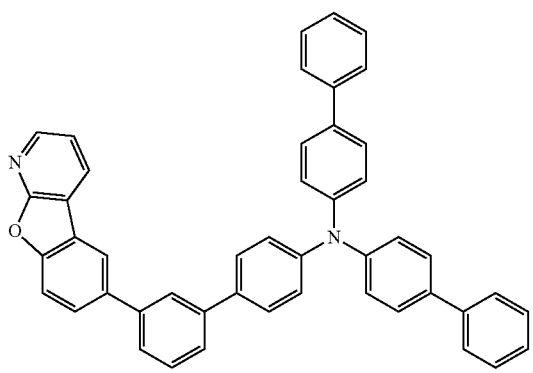
43
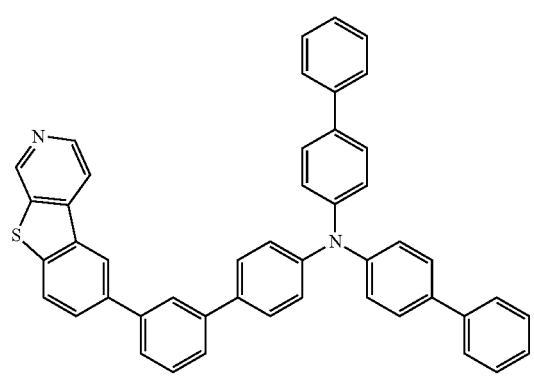
44
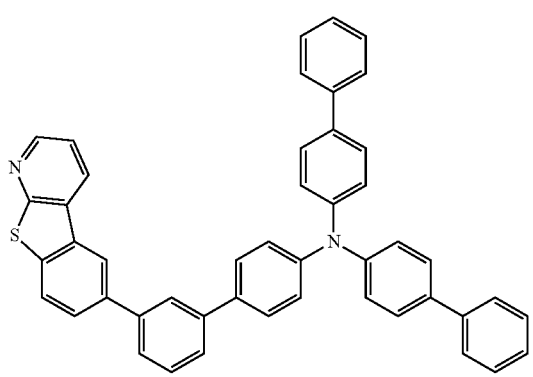

45
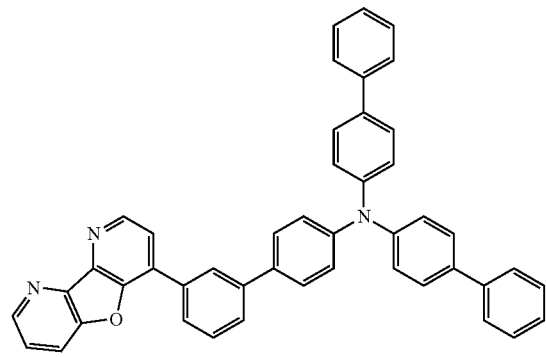
46
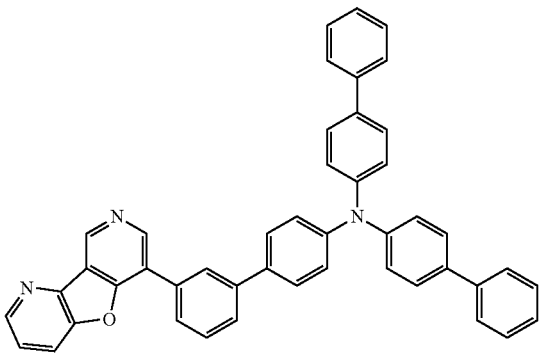
47
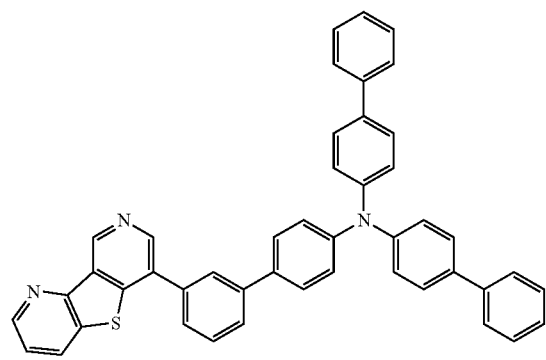
48
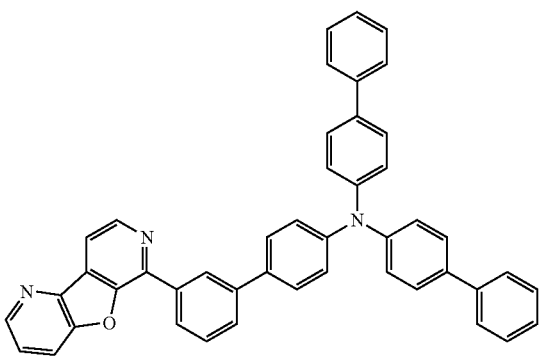
49
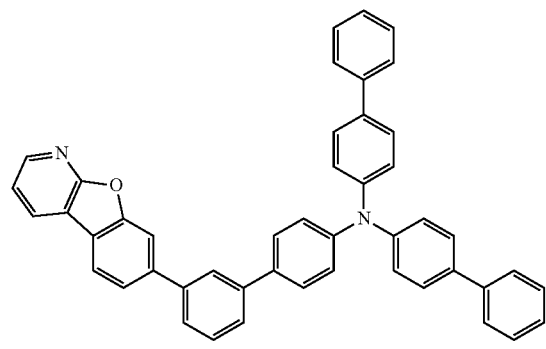
50
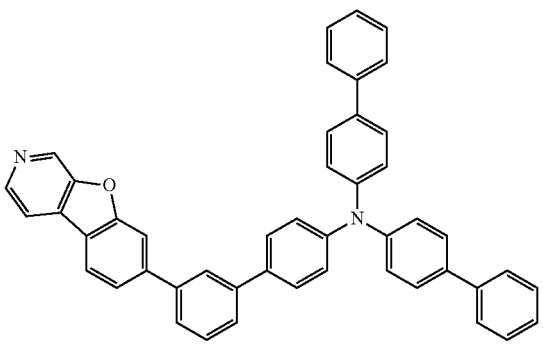
51
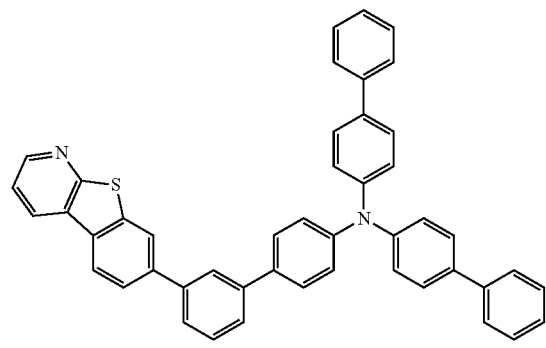
52
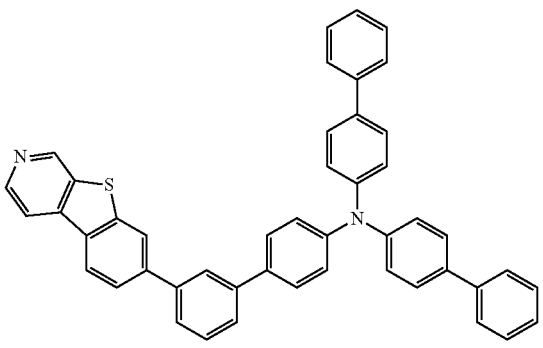

-continued
53
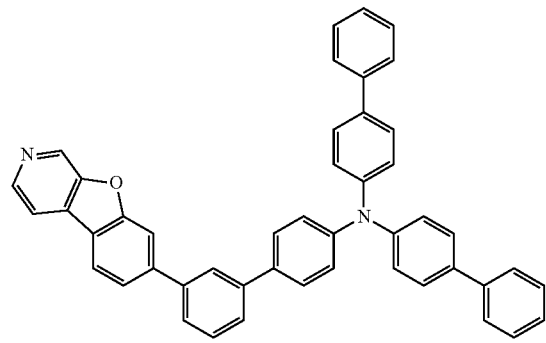
54
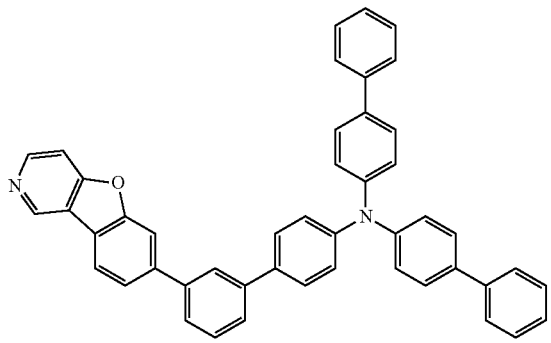
55
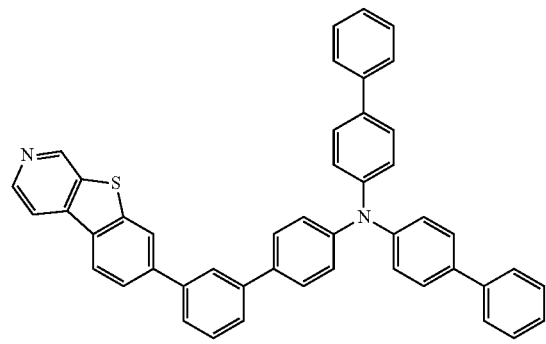
56
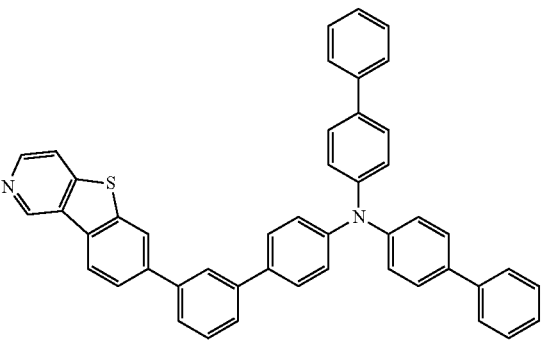
57
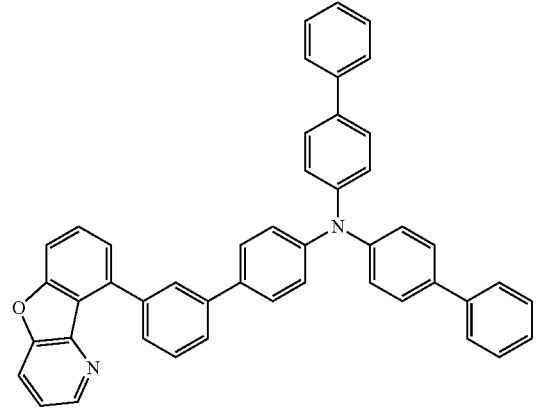
58
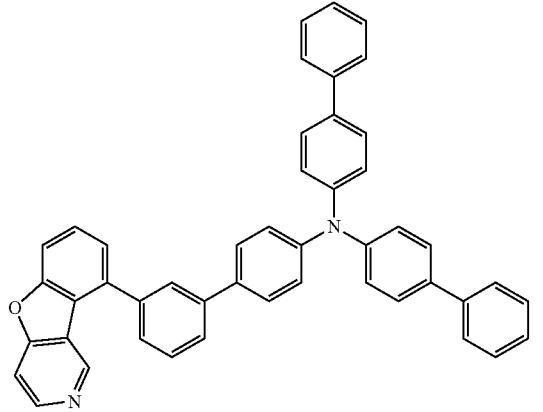
59
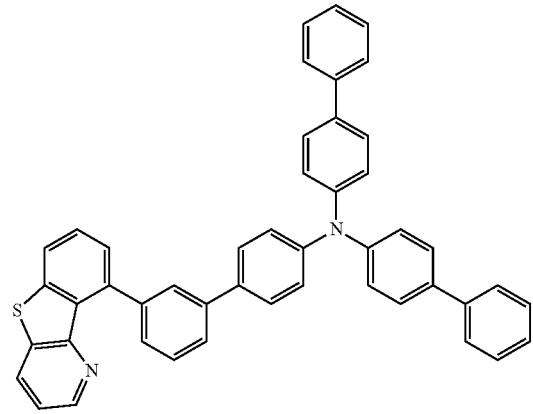
60
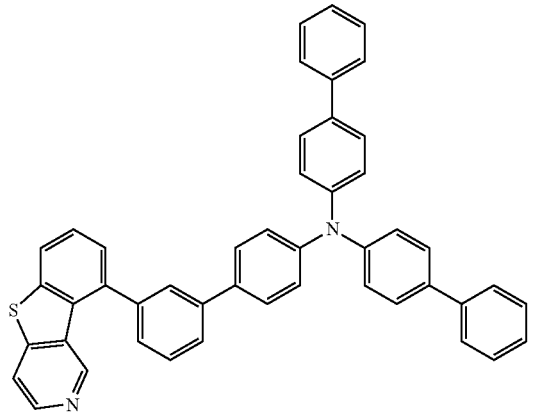

-continued
61
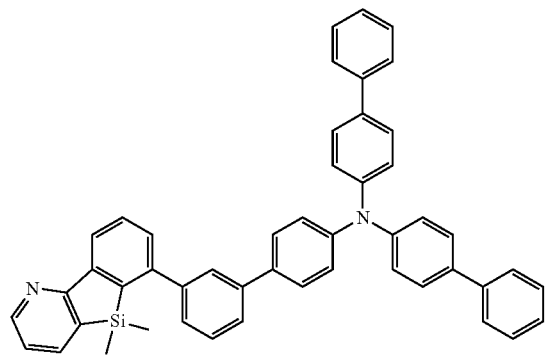
62
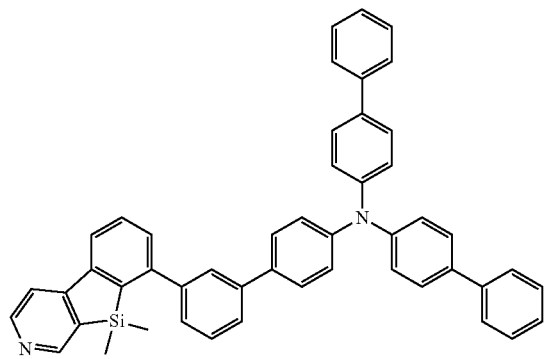
63
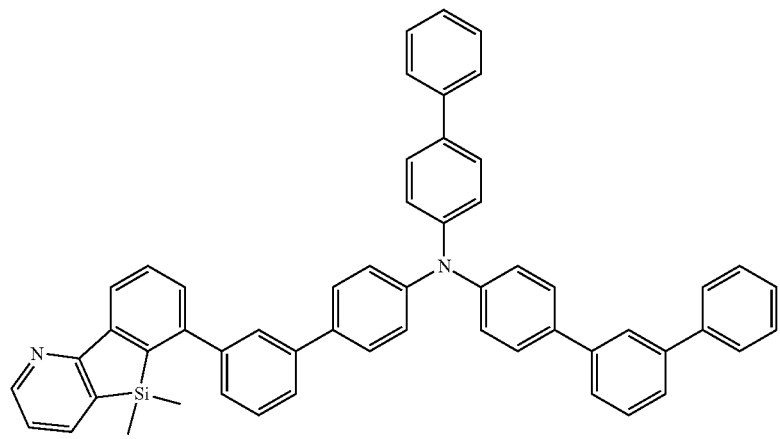
64
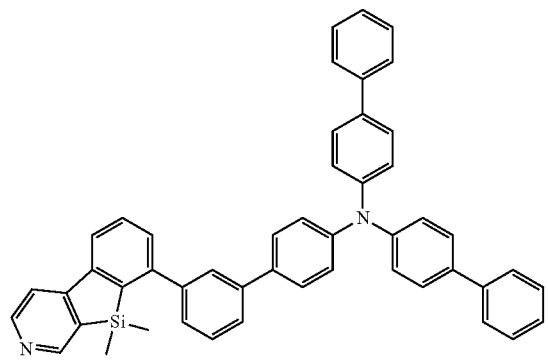
65
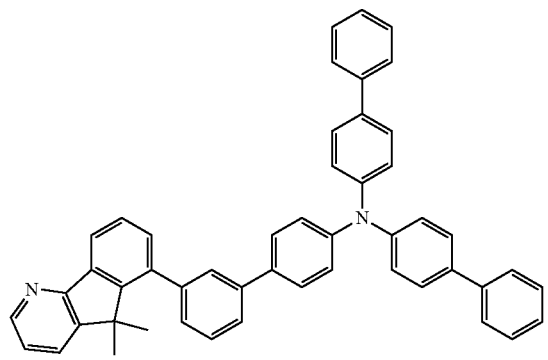
66
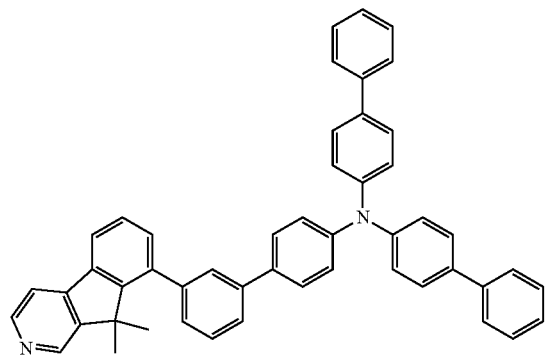
67
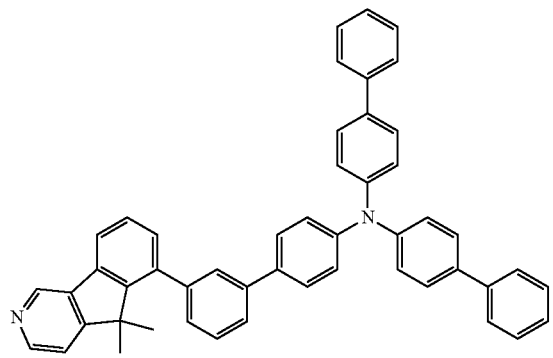

-continued
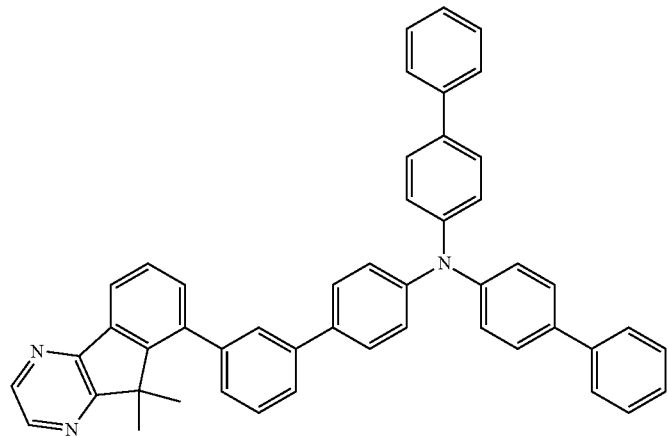
68
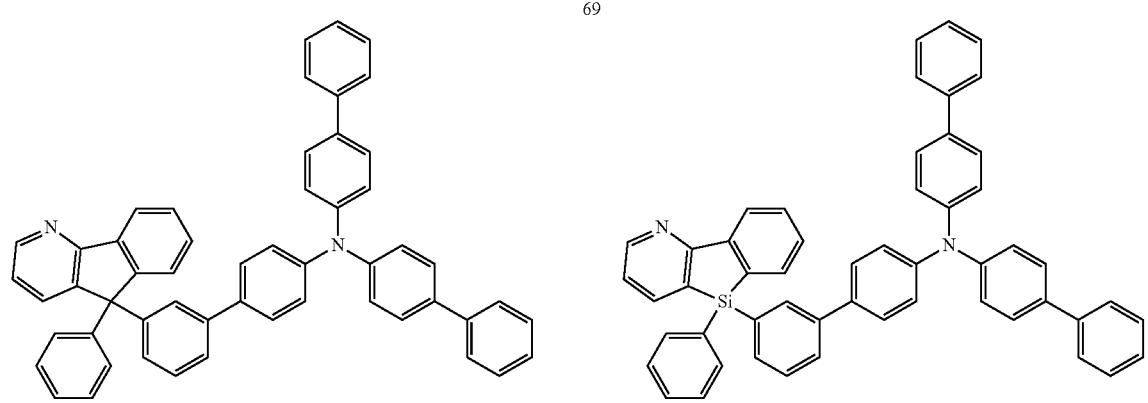
69  70
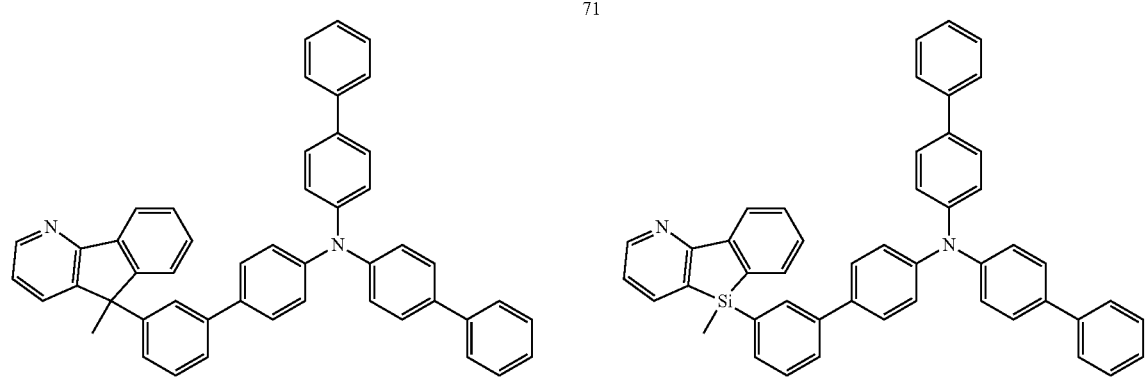
71  72
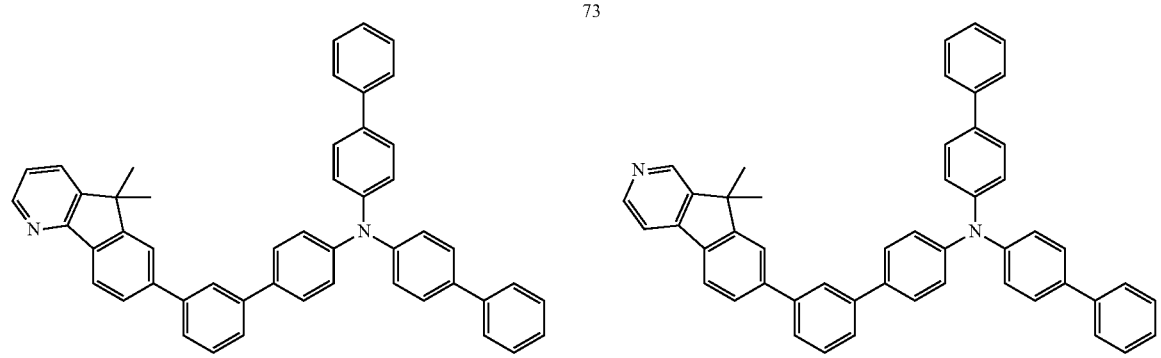
73  74

-continued
75
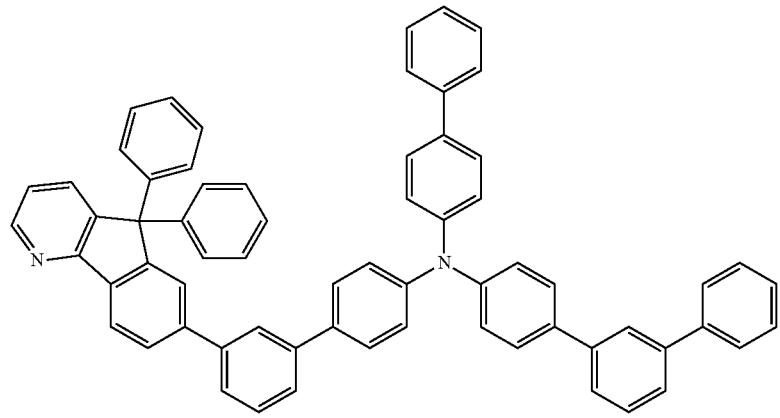
76
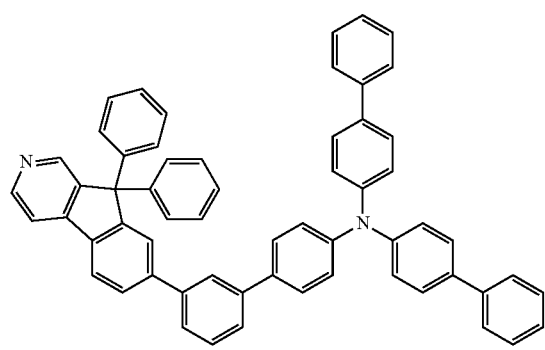
77
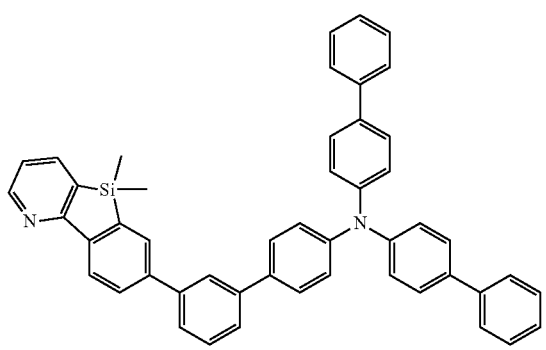
78
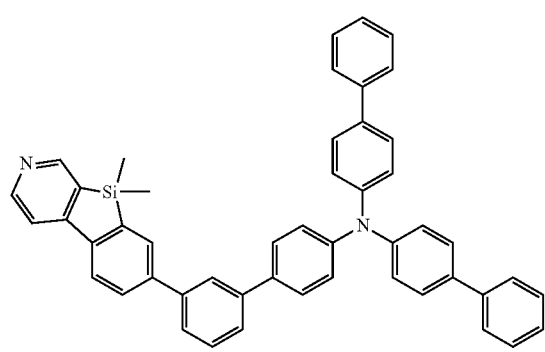
79
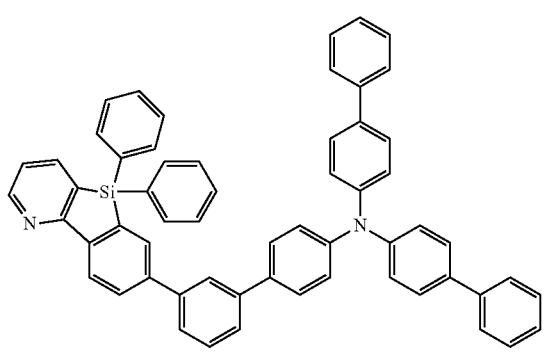
80
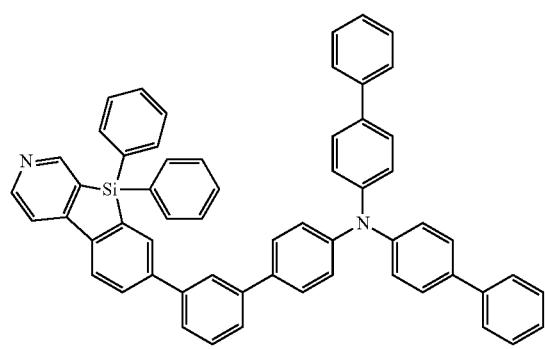
81
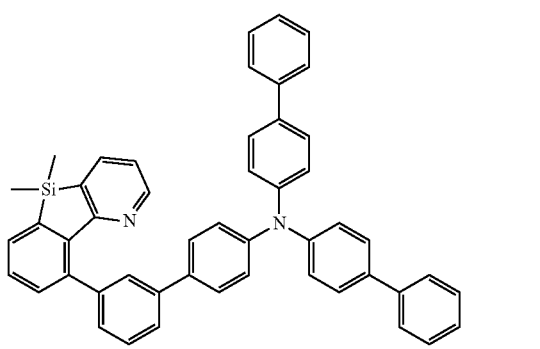

-continued

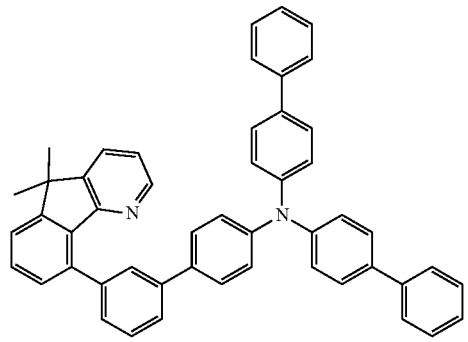
82

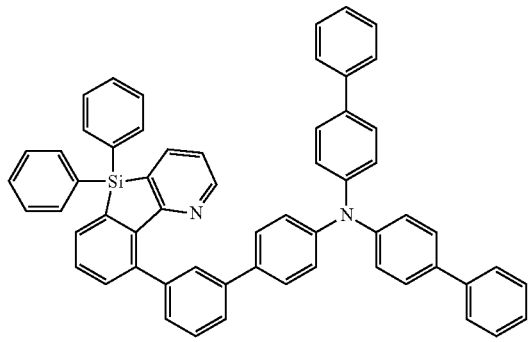
83

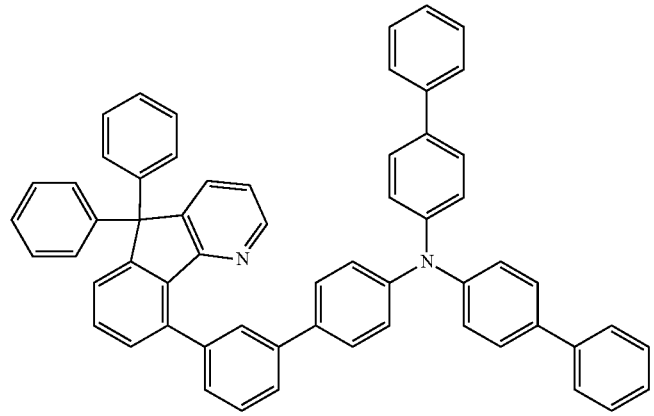
84

The material for an organic EL device according to embodiments of the present disclosure may be used in at least one layer of stacking layers disposed between the emission layer and the anode of an organic EL device. Accordingly, the amorphous properties of the material may be improved, the mobility of charge may be increased, and the long life of the organic EL device may be realized. In addition, since the electron tolerance of the material increases, durability may be increased, and the life of the organic EL device may be increased further.

A layer including the material for an organic EL device according to embodiments of the present disclosure may preferably be adjacent to (e.g., physically contacting) the emission layer among stacking layers disposed between the emission layer and the anode of the organic EL device. The deterioration due to electrons of a layer disposed between the layer including the material for an organic EL device according to embodiments of the present disclosure and the anode may be effectively restrained or reduced by disposing the layer including the material for an organic EL device according to embodiments of the present disclosure adjacent to (e.g., physically contacting) the emission layer.

(Organic EL Device)

An organic EL device using a material for an organic EL device according to embodiments of the present disclosure will be explained with reference to the drawings. FIG. 1 is a schematic diagram illustrating an organic EL device 100 according to an embodiment of the present disclosure. The organic EL device 100 may include, for example, a substrate 102, an anode 104, a hole injection layer 106, a hole transport layer 108, an emission layer 110, an electron transport layer 112, an electron injection layer 114 and a cathode 116. In an embodiment, the material for an organic EL device according to embodiments of the present disclosure may be used in at least one layer of stacking layers disposed between the emission layer and the anode.

Here, an example in which the material for an organic EL device according to embodiments of the present disclosure is used in the hole transport layer 108 will be described as an embodiment.

The substrate 102 may be a transparent glass substrate, a semiconductor substrate formed using silicon, a flexible substrate of a resin, and/or the like.

The anode 104 may be disposed on the substrate 102 and may be formed using indium tin oxide (ITO), indium zinc oxide (IZO), and/or the like.

The hole injection layer (HIL) 106 may be formed using any suitable material available in the art, and may be formed to a thickness in a range from about 10 nm to about 150 nm. For example, triphenylamine-containing poly ether ketone (TPAPEK), 4-isopropyl-4'-methyldiphenyliodoniumtetrakis (pentafluorophenyl)borate (PPBI), N,N'-diphenyl-N,N'-bis-[4-(phenyl-m-trile-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate (PEDOT/PSS), polyaniline/camphorsulfonic acid (PANI/CSA), polyaniline/poly(4-styrenesulfonate (PANI/PSS), and/or the like, may be included.

The hole transport layer (HTL) 108 may be formed on the hole injection layer 106 using the material for an organic EL device according to embodiments of the present disclosure to a thickness in a range from about 10 nm to about 150 nm. The hole transport layer 108 including the material for an organic EL device according to embodiments of the present disclosure may be formed by a vacuum evaporation method (e.g., an evaporation deposition method).

The emission layer (EL) 110 may be formed on the hole transport layer 108 using any suitable host material available in the art, and may be formed to a thickness in a range from about 10 nm to about 60 nm. The host material used in the emission layer 110 may include, for example, tris(8-quinolinolato)aluminum (Alq3), 4,4'-N,N'-dicarbazole-biphenyl (CBP), poly(n-vinylcarbazole) (PVK), 9,10-di(naphthalene-2-yl)anthracene (ADN), 4,4',4''-tris(N-carbazolyl)triphenylamine (TCTA), 1,3,5-tris(N-phenylbenzimidazole-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dmCBP), and/or the like.

The emission layer 110 may include as a dopant material, styryl derivatives (such as 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalene-2-yl)vinyl)phenyl-N-phenylbenzeneamine (N-BDAVBI)), perylene and the derivatives thereof (such as 2,5,8,11-tetra-t-butylperylene (TBPe)), pyrene and the derivatives thereof (such as 1,1-dipyrene, 1,4-dipyrenylbenzene, 1,4-bis(N,N-diphenylamino)pyrene), and/or the like, without limitation.

The electron transport layer (ETL) 112 may be formed on the emission layer 110 to a thickness in a range from about 15 nm to about 50 nm using tris(8-hydroxyquinolinato)aluminum (Alq3) or a material having a nitrogen-containing aromatic ring (for example, a material including a pyridine ring such as 1,3,5-tri[(3-pyridyl)-phen-3-yl]benzene, a material including a triazine ring such as 2,4,6-tris(3'-(pyridine-3-yl)biphenyl-3-yl)1,3,5-triazine, and/or a material including an imidazole derivative such as 2-(4-N-Phenyl-benzoimidazolyl-1-ylphenyl)-9,10-dinaphthylanthracene).

The electron injection layer (EIL) 114 may be formed on the electron transport layer 112 to a thickness in a range from about 0.3 nm to about 9 nm using a material including, for example, lithium fluoride (LiF), lithium-8-quinolinato (Liq), and/or the like.

The cathode 116 may be disposed on the electron injection layer 114 and may be formed using a metal such as aluminum (Al), silver (Ag), lithium (Li), magnesium (Mg) and/or calcium (Ca), and/or a transparent material such as ITO and/or IZO.

Each electrode and each layer constituting the organic EL device according to embodiments of the present disclosure as described above may be formed by selecting an appropriate or suitable layer forming method according to a material such as a vacuum evaporation method (e.g., an evaporation deposition method), a sputtering method, various suitable coating methods, and/or the like. In addition, the hole transport layer 108 formed using the material for an organic EL device according to embodiments of the present disclosure may be formed by the vacuum evaporation method (e.g., an evaporation deposition method).

In the organic EL device 100 according to embodiments of the present disclosure, a hole transport layer capable of realizing long life may be formed using the material for an organic EL device according to embodiments of the present disclosure.

In addition, in the organic EL device according to embodiments of the present disclosure, the material for an organic EL device according to embodiments of the present disclosure may be used as a material of the hole injection layer. As described above, an organic EL device with long life may be manufactured by using the material for an organic EL device according to embodiments of the present disclosure in at least one layer of stacking layers disposed between the emission layer and the anode.

In addition, the material for an organic EL device according to embodiments of the present disclosure may also be applied in an organic EL device of an active matrix type (or kind) using a TFT.

(Manufacturing Method)

The material for an organic EL device according to embodiments of the present disclosure may be synthesized, for example, as follows.

Synthetic Method of Compound 1

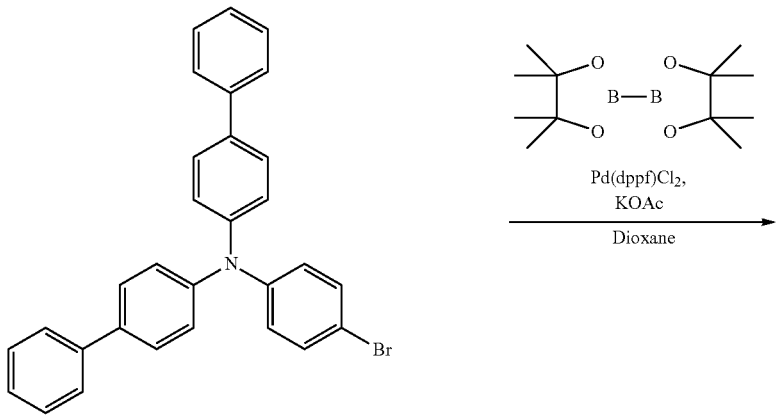

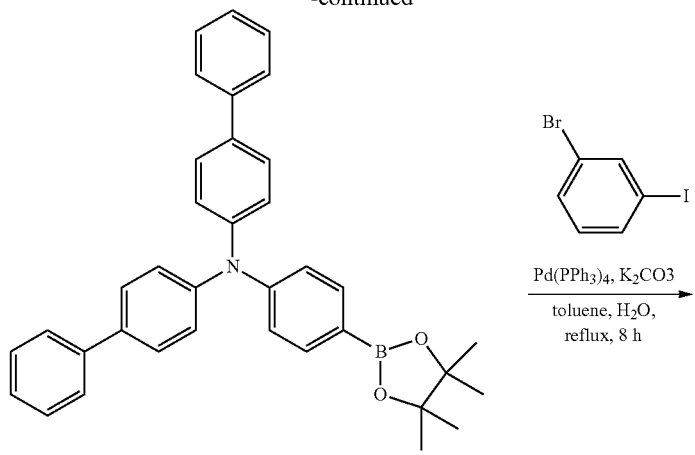

A
(98%)

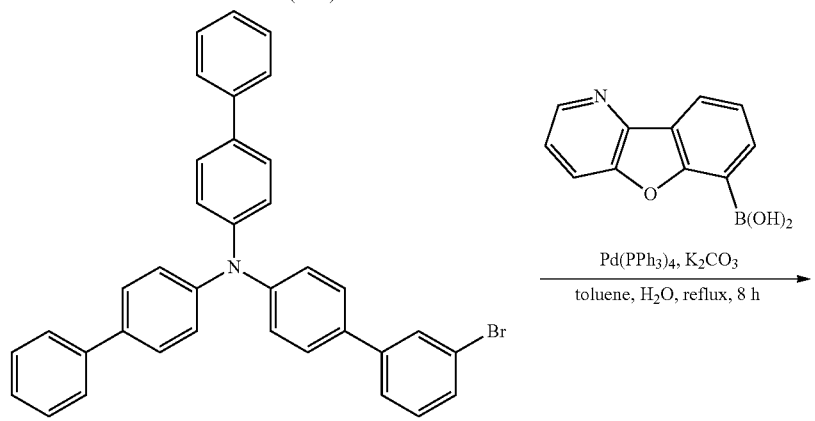

B
(88%)

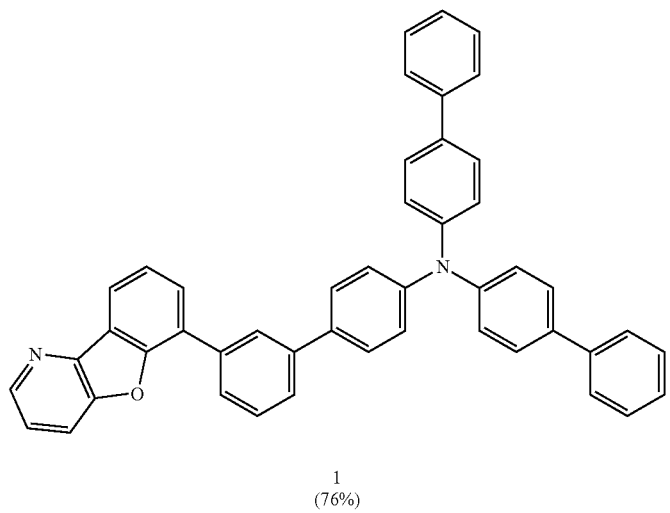 [SMILES: c1ccc(-c2ccc(N(c3ccc(-c4ccccc4)cc3)c3ccc(-c4cccc(-c5cccc6c5oc5cccnc56)c4)cc3)cc2)cc1]

1
(76%)

(Synthesis of Compound A)

Under an Ar atmosphere, 53.8 g of N-[1,1'-biphenyl]-4-yl-N-(4-bromophenyl)-[1,1'-biphenyl]-4-amine, 6.46 g of Pd(dppf)Cl$_2$.CH$_2$Cl$_2$, 33.3 g of KOAc and 33.0 g of bis(pinacolato)diboron were added to a 2 L flask, followed by degassing under vacuum and stirring in a dioxane solvent at about 100° C. for about 12 hours. Then, the solvent was distilled (evaporated off), CH$_2$Cl$_2$ and water were added thereto, an organic phase was separated, and magnesium sulfate and activated clay were added thereto. Filtration with suction was performed, and solvent was distilled (evaporated off). The crude product thus obtained was separated by silica gel column chromatography (a mixture solvent of dichloromethane/hexane) to produce 56.8 g (Yield 98%) of Compound A as a white solid. The molecular weight of Compound A measured by Fast Atom Bombardment Mass Spectrometry (FAB-MS) was 523.

(Synthesis of Compound B)

Under an Ar atmosphere, 10.0 g of Compound A, 6.00 g of 1-iodo-3-bromobenzene, 1.54 g of Pd(PPh$_3$)$_4$ and 5.25 g of potassium carbonate were added to a 300 mL, three-necked flask, followed by heating and stirring in a mixture solvent of 450 mL of toluene and 60 mL of water at about 90° C. for about 8 hours. After air cooling, water was added thereto, an organic layer was separated, and solvent was distilled (evaporated off). The crude product thus obtained was separated by silica gel column chromatography (a mixture solvent of dichloromethane and hexane) and recrystallized using a mixture solvent of toluene and hexane to produce 9.29 g (Yield 88%) of Compound B as a white solid. The molecular weight of Compound B measured by FAB-MS was 553.

(Synthesis of Compound 1)

Under an Ar atmosphere, 2.00 g of Compound B, 0.81 g of benzofuro[3,2-b]pyridine-10-boronic acid, 0.42 g of Pd(PPh$_3$)$_4$ and 1.11 g of potassium carbonate were added to a 300 mL, three-necked flask, followed by heating and stirring in a mixture solvent of 90 mL of toluene and 40 mL of water at about 90° C. for about 8 hours. After air cooling, water was added thereto, an organic layer was separated, and solvent was distilled (evaporated off). The crude product thus obtained was separated by silica gel column chromatography (a mixture solvent of dichloromethane and hexane) and recrystallized using a mixture solvent of toluene and hexane to produce 1.76 g (Yield 76%) of Compound 1 as a white solid. The molecular weight of Compound 1 measured by FAB-MS was 640. In addition, the chemical shift values (δ) of Compound 1 measured by proton Nuclear Magnetic Spectroscopy with a CDCl$_3$ standard ($^1$H-NMR (CDCl$_3$)) were 8.47-8.41 (m, 7H), 8.20 (d, 1H, J=7.80 Hz), 8.07-7.98 (m, 3H), 7.57-7.50 (m, 11H), 7.45-7.34 (m, 3H), 6.96 (d, 1H, J=7.76 Hz), 6.90-6.87 (m, 2H), 6.59 (d, 2H, J=7.82 Hz), and 6.58 (d, 1H, J=7.70 Hz).

In addition, the material for an organic EL device according to embodiments of the present disclosure may be synthesized, for example, as follows.

(Synthesis of Compound 2)

Compound 2 was synthesized by substantially the same method as the synthetic method of Compound 1 except for using benzofuro[2,3-c]pyridine-10-boronic acid instead of benzofuro[3,2-b]pyridine-10-boronic acid. In addition, the chemical shift values (δ) of Compound 2 measured by $^1$H-NMR (CDCl$_3$) were 8.45-8.41 (m, 7H), 8.30 (d, 1H, J=7.80 Hz), 8.07-7.98 (m, 3H), 7.57-7.51 (m, 11H), 7.48-7.38 (m, 3H), 7.08 (d, 1H, J=7.76 Hz), 6.99-6.91 (m, 2H), 6.77 (d, 2H, J=7.82 Hz), and 6.68 (d, 1H, J=7.70 Hz).

(Synthesis of Compound 3)

Compound 3 was synthesized by substantially the same method as the synthetic method of Compound 1 except for using benzofuro[2,3-b]pyridine-10-boronic acid instead of benzofuro[3,2-b]pyridine-10-boronic acid. In addition, the chemical shift values (δ) of Compound 3 measured by $^1$H-NMR (CDCl$_3$) were 8.52-8.45 (m, 7H), 8.40 (d, 1H, J=7.90 Hz), 8.17-7.88 (m, 3H), 7.67-7.55 (m, 11H), 7.42-7.28 (m, 3H), 6.88 (d, 1H, J=7.56 Hz), 6.90-6.87 (m, 2H), 6.59 (d, 2H, J=7.82 Hz), and 6.48 (d, 1H, J=7.60 Hz).

(Synthesis of Compound 5)

Compound 5 was synthesized by substantially the same method as the synthetic method of Compound 1 except for using benzothieno[3,2-b]pyridine-10-boronic acid instead of benzofuro[3,2-b]pyridine-10-boronic acid. In addition, the chemical shift values (δ) of Compound 5 measured by $^1$H-NMR (CDCl$_3$) were 8.35-8.31 (m, 7H), 8.17 (d, 1H, J=7.80 Hz), 8.07-8.00 (m, 3H), 7.77-7.59 (m, 11H), 7.44-7.29 (m, 3H), 7.08 (d, 1H, J=7.76 Hz), 6.90-6.85 (m, 2H), 6.77 (d, 2H, J=7.88 Hz), and 6.59 (d, 1H, J=7.90 Hz).

(Synthesis of Compound 33)

Compound 33 was synthesized by substantially the same method as the synthetic method of Compound 1 except for using benzofuro[2,3-b]pyridine-10-boronic acid instead of benzofuro[3,2-b]pyridine-10-boronic acid. In addition, the chemical shift values (δ) of Compound 33 measured by $^1$H-NMR (CDCl$_3$) were 8.45-8.40 (m, 7H), 8.21 (d, 1H, J=7.80 Hz), 8.06-7.97 (m, 3H), 7.56-7.50 (m, 14H), 6.98 (d, 1H, J=7.76 Hz), 6.90-6.87 (m, 2H), 6.69 (d, 2H, J=7.82 Hz), and 6.55 (d, 1H, J=7.70 Hz).

(Synthesis of Compound 45)

Compound 45 was synthesized by substantially the same method as the synthetic method of Compound 1 except for using furo[3,2-b:4,5-b']pyridine-10-boronic acid instead of benzofuro[3,2-b]pyridine-10-boronic acid. In addition, the chemical shift values (δ) of Compound 45 measured by $^1$H-NMR (CDCl$_3$) were 8.68-8.60 (m, 6H), 8.35 (d, 1H, J=7.60 Hz), 8.07-7.98 (m, 3H), 7.77-7.50 (m, 11H), 7.40-7.28 (m, 3H), 6.98 (d, 1H, J=7.76 Hz), 6.90-6.80 (m, 2H), 6.70 (d, 2H, J=7.82 Hz), and 6.59 (d, 1H, J=7.80 Hz).

(Synthesis of Compound 49)

Compound 49 was synthesized by substantially the same method as the synthetic method of Compound 1 except for using benzofuro[3,2-b]pyridine-9-boronic acid instead of benzofuro[3,2-b]pyridine-10-boronic acid. In addition, the chemical shift values (δ) of Compound 49 measured by $^1$H-NMR (CDCl$_3$) were 8.55-8.41 (m, 7H), 8.23 (d, 1H, J=7.90 Hz), 8.05-7.95 (m, 3H), 7.67-7.54 (m, 11H), 7.44-7.38 (m, 3H), 7.11 (d, 1H, J=7.74 Hz), 6.90-6.83 (m, 2H), 6.71 (d, 2H, J=7.82 Hz), and 6.59 (d, 1H, J=7.85 Hz).

(Synthesis of Compound 57)

Compound 57 was synthesized by substantially the same method as the synthetic method of Compound 1 except for using benzofuro[3,2-b]pyridine-7-boronic acid instead of benzofuro[3,2-b]pyridine-10-boronic acid. In addition, the chemical shift values (δ) of Compound 57 measured by $^1$H-NMR (CDCl$_3$) were 8.36-8.31 (m, 7H), 8.22 (d, 1H, J=7.20 Hz), 8.05-7.92 (m, 3H), 7.67-7.58 (m, 11H), 7.40-7.32 (m, 3H), 7.08 (d, 1H, J=7.76 Hz), 6.80-6.71 (m, 2H), 6.59 (d, 2H, J=7.82 Hz), and 6.46 (d, 1H, J=7.80 Hz).

Figure 2:
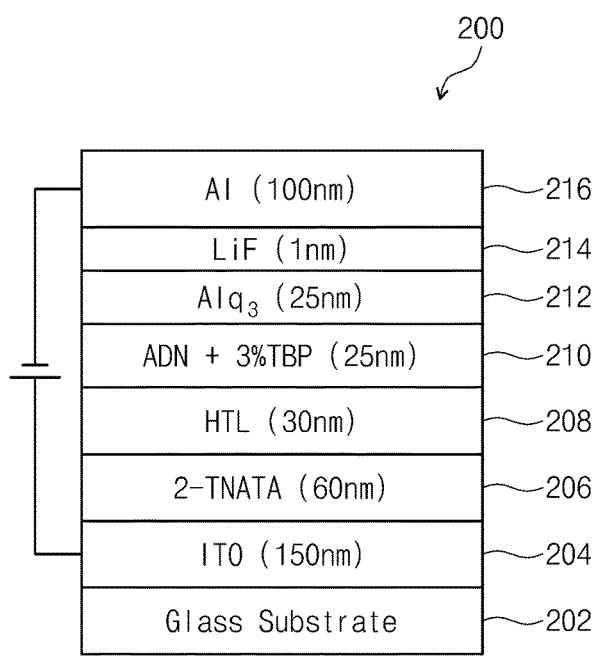
FIG. 2 is a schematic diagram illustrating an organic EL device 200 according to an embodiment of the present disclosure.

Organic EL devices of Examples 1 to 8 were manufactured using Compound 1, Compound 2, Compound 3, Compound 5, Compound 33, Compound 45, Compound 49 and Compound 57, respectively, as the hole transport materials of organic EL devices as described with respect to FIG. 2.

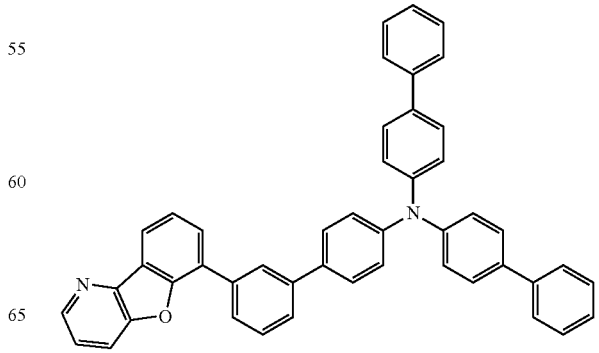

2
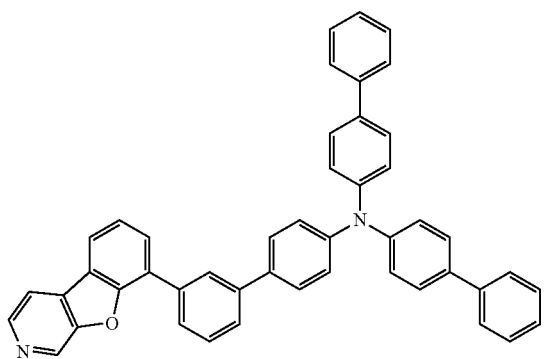
3
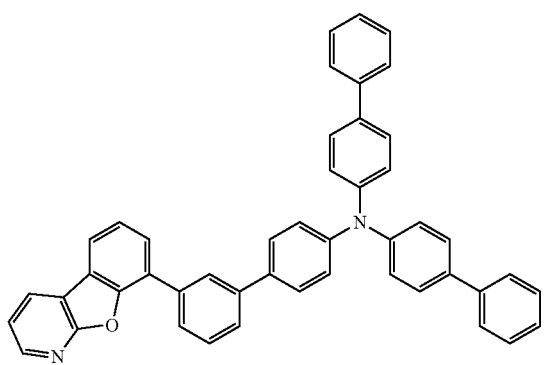
5
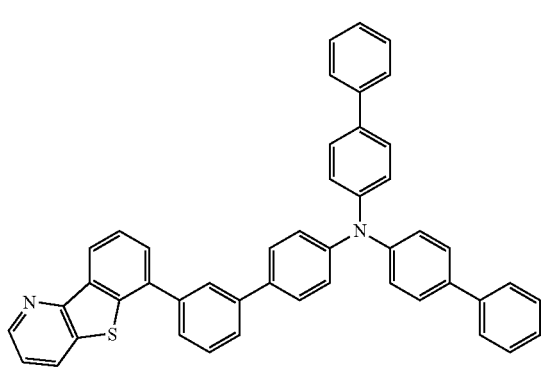
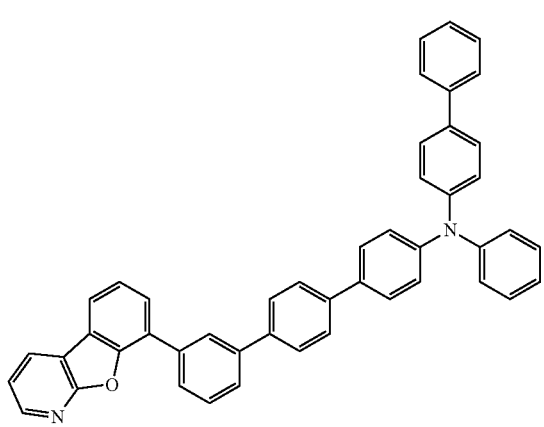
45
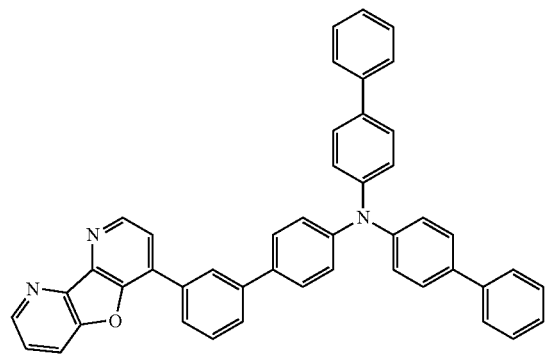
49
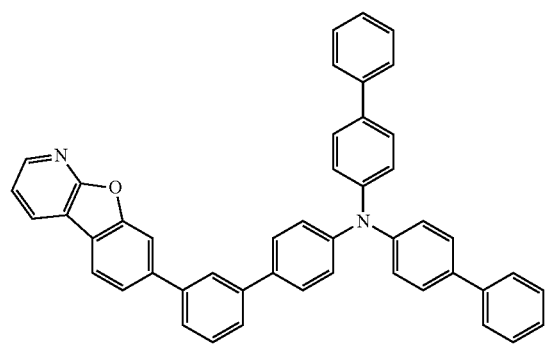
57
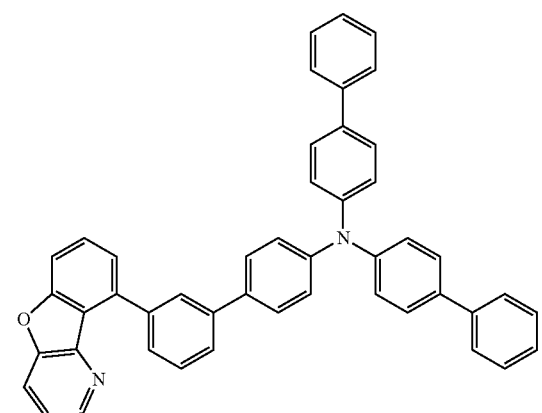
In addition, organic EL devices of Comparative Examples 1 to 3 were manufactured in substantially the same manner as described with respect to Examples 1 to 8 except for using the following Comparative Compounds C1 to C3, respectively, as the hole transport materials of a hole transport layer.

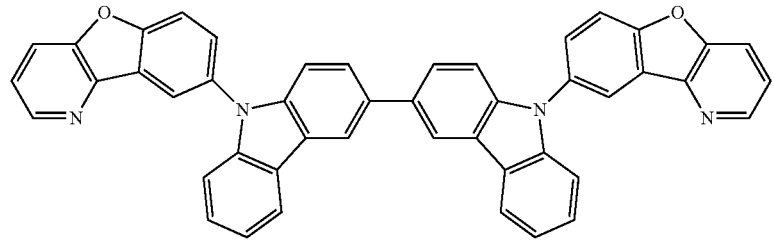

C1

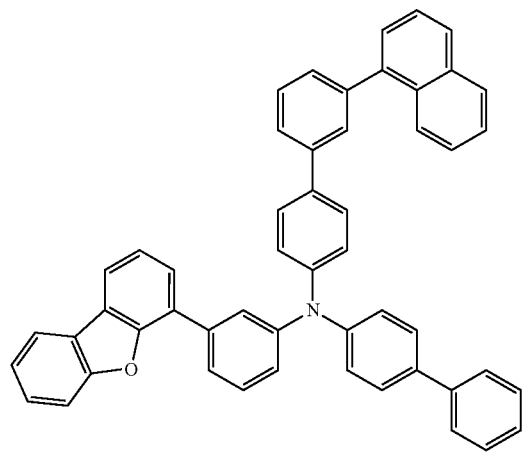

C2

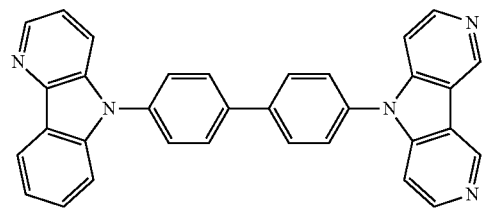

C3

An organic EL device 200 according to embodiments of the present disclosure is shown in FIG. 2. In this embodiment, a transparent glass substrate was used as a substrate 202, an anode 204 was formed using ITO to a layer thickness of about 150 nm, a hole injection layer 206 was formed using 2-TNATA to a layer thickness of about 60 nm, a hole transport layer 208 was formed to a layer thickness of about 30 nm, an emission layer 210 was formed using ADN doped with 3% TBP to a layer thickness of about 25 nm, an electron transport layer 212 was formed using Alq3 to a layer thickness of about 25 nm, an electron injection layer 214 was formed using LiF to a layer thickness of about 1 nm, and a cathode 216 was formed using Al to a layer thickness of about 100 nm.

For the organic EL devices 200 thus manufactured, a driving voltage and half life were evaluated. The voltage was obtained at about 10 mA/cm$^2$, and the half life was represented by time necessary for decreasing luminance to half (50%) from an initial luminance of about 1,000 cd/m$^2$. The evaluation results are shown in Table 1.

TABLE 1

| Manufacturing examples of device | Electron transport layer | Voltage (V) | Half Life LT50 (h) |
|---|---|---|---|
| Example 1 | Compound 1 | 5.7 | 2,500 |
| Example 2 | Compound 2 | 5.8 | 2,450 |
| Example 3 | Compound 3 | 5.6 | 2,500 |
| Example 4 | Compound 5 | 5.7 | 2,400 |
| Example 5 | Compound 33 | 5.7 | 2,450 |
| Example 6 | Compound 45 | 5.9 | 2,300 |
| Example 7 | Compound 49 | 5.9 | 2,350 |
| Example 8 | Compound 57 | 5.7 | 2,350 |
| Comparative Example 1 | Comparative Compound C1 | 7.3 | 1,700 |
| Comparative Example 2 | Comparative Compound C2 | 7.1 | 1,500 |
| Comparative Example 3 | Comparative Compound C3 | 7.6 | 1,300 |

Referring to the results in Table 1, the organic EL devices of Examples 1 to 8 were recognized to have longer life when compared to those of Comparative Examples 1 to 3. In Examples 1 to 8, the electron tolerance of the hole transport layer was improved, and the life was increased by introducing an electron accepting azadibenzoheterole part to a hole transport amine (e.g., by including an electron accepting azadibenzoheterole group in a hole transport amine).

From the results in Table 1, it would be recognized that a case of using the material for an organic EL device of embodiments of the present disclosure as the hole transport material provided longer life than a case of using the comparative compound as the hole transport material. In the material for an organic EL device of embodiments of the present disclosure, the azadibenzoheterole part (the azadibenzoheterole group) was introduced (included) at the meta (m) position of a phenylene group combined with an amine. Thus, the properties of the amine such as long life may be maintained, the amorphous properties of the material may be improved, and long life may be realized. In addition, by introducing (including) the electron accepting azadibenzoheterole part (the electron accepting azadibenzoheterole group), the electron tolerance of the material for an organic EL device may be increased, the durability of the material may be improved, and the life of the organic EL device may be increased further.

In a material for an organic EL device according to embodiments of the present disclosure, the amorphous properties of the material may be improved, and the electron tolerance thereof may be improved by introducing (including) an azadibenzoheterole part (an azadibenzoheterole group) at the meta (m) position of a phenylene group combined with an amine. Thus, the mobility of charge may be increased, and long life may be realized. In addition, since the material for an organic EL device according to embodiments of the present disclosure has a wide energy gap, application to a green emission region and a red emission region may be possible.

The above-disclosed subject matter is to be considered illustrative and not restrictive, and the appended claims are intended to cover all such modifications, enhancements, and other embodiments that fall within the true spirit and scope of the inventive concept. Thus, to the maximum extent allowed by law, the scope of the inventive concept is to be determined by the broadest permissible interpretation of the following claims and their equivalents, and shall not be restricted or limited by the foregoing detailed description.

What is claimed is:

1. A material for an organic electroluminescent (EL) device comprising a material represented by Formula (3):

Formula 3

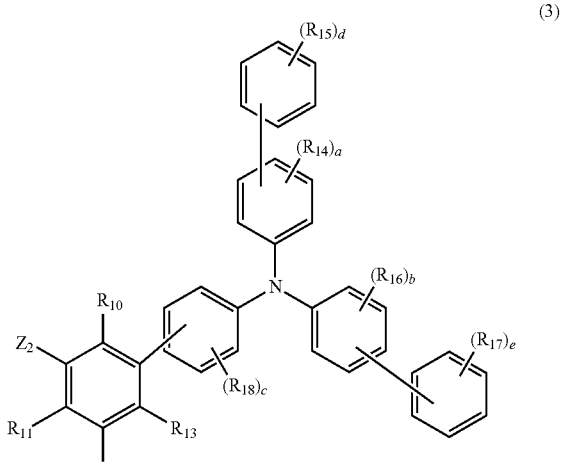

wherein $R_{10}$ to $R_{18}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom, a to c are each independently an integer from 0 to 4, d and e are each independently an integer from 0 to 5, and $Z_2$ is a monovalent group represented by Formula (4):

Formula 4

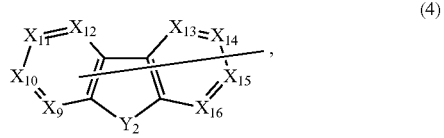

wherein $X_9$ to $X_{16}$ are each independently N or $CR_{19}$, at least one of $X_9$ to $X_{16}$ is N, $Y_2$ is O, S, $CR_{20}R_{21}$ or $SiR_{22}R_{23}$, and $R_{19}$ to $R_{23}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom.

2. A material for an organic electroluminescent (EL) device comprising a material represented by one of Compounds 1 to 84:

| 1 | 2 |
|---|---|
| 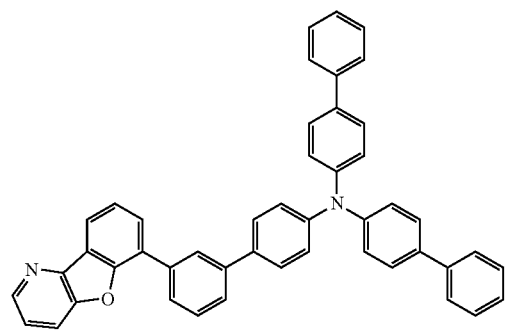 | 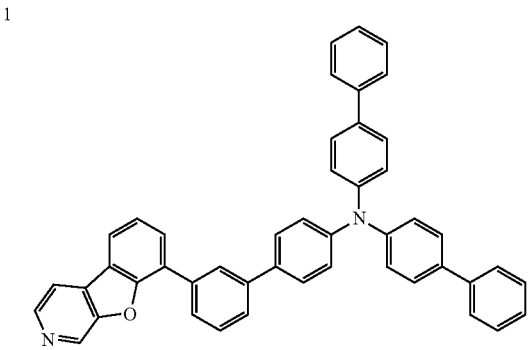 |
| 3 | 4 |
| 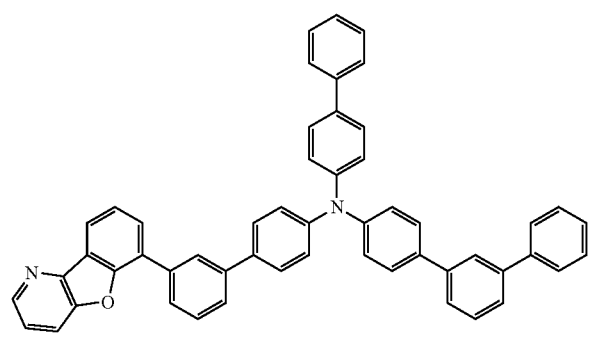 | 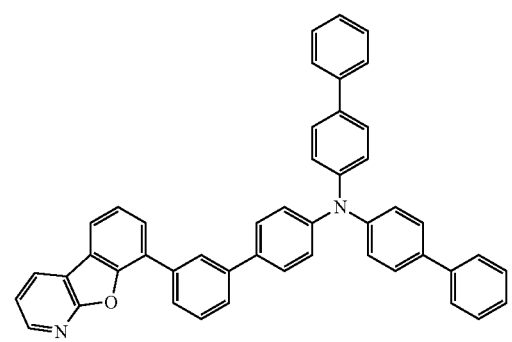 |
| 5 | 6 |
| 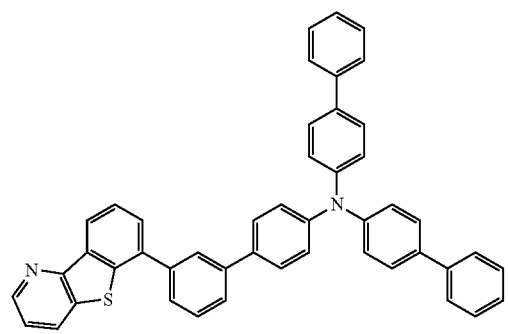 | 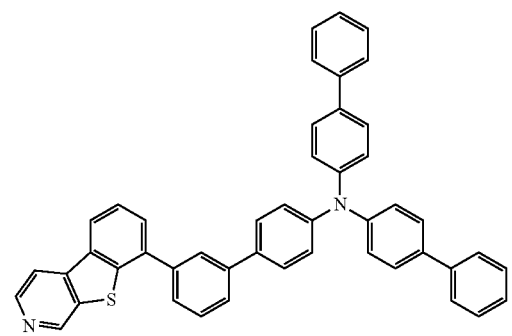 |
| 7 | 8 |
| 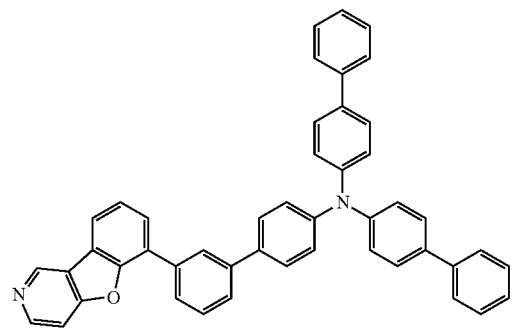 | 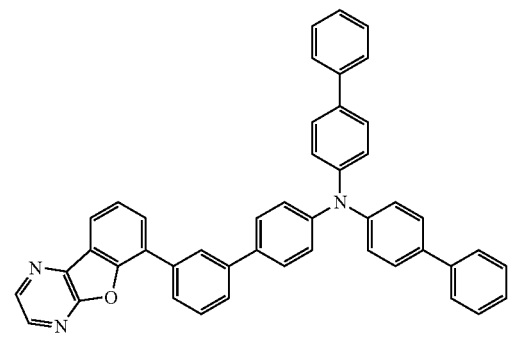 |

-continued
9
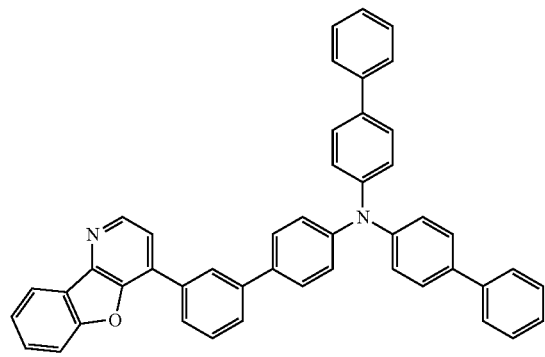
10
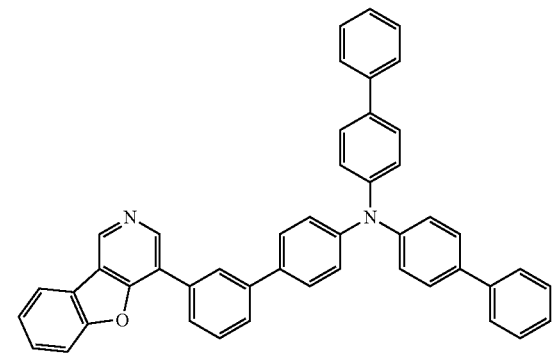
11
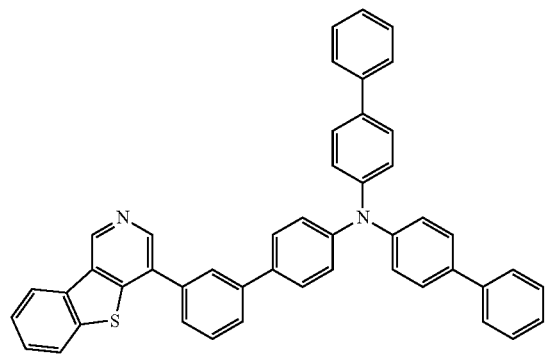
12
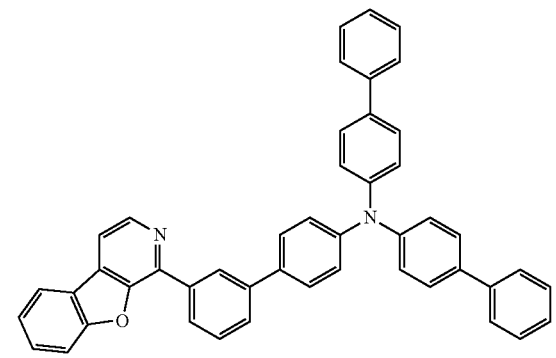
13
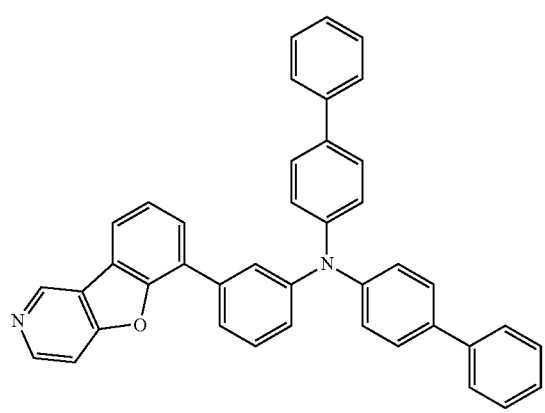
14
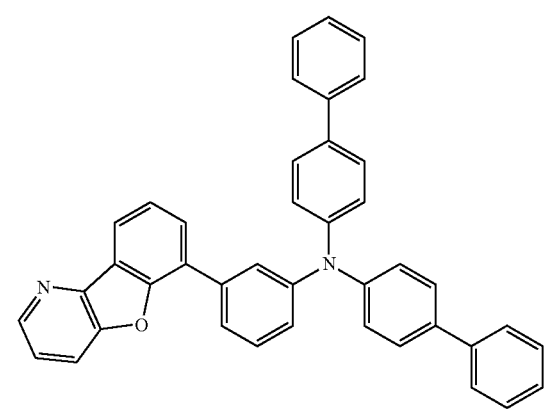
15
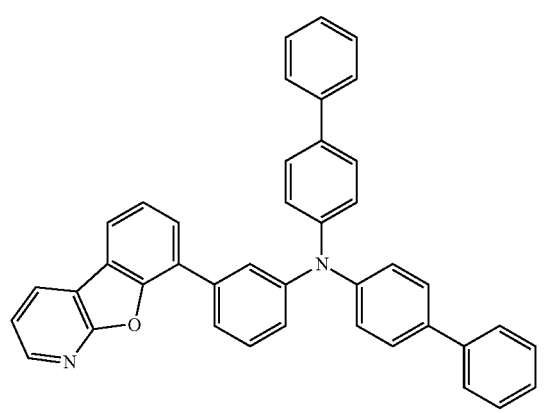
16
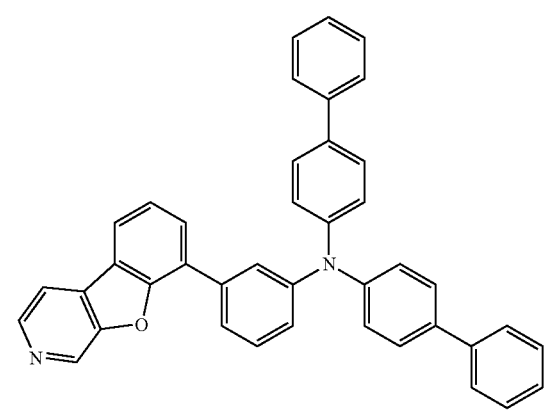

-continued
17
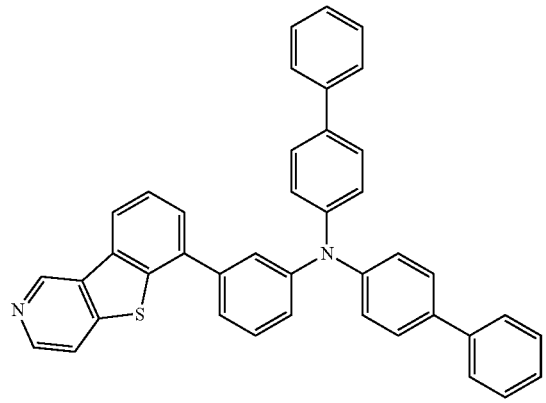
18
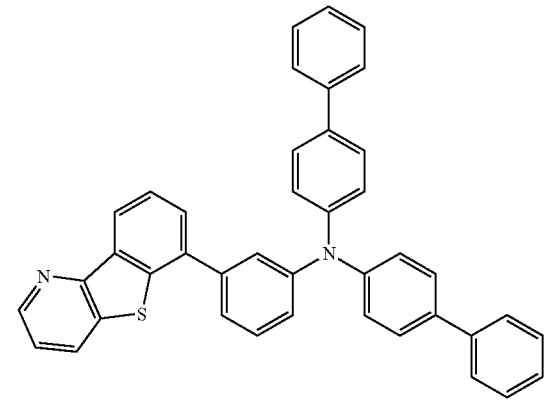
19
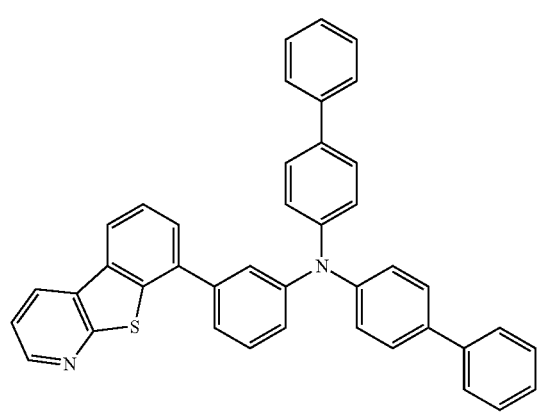
20
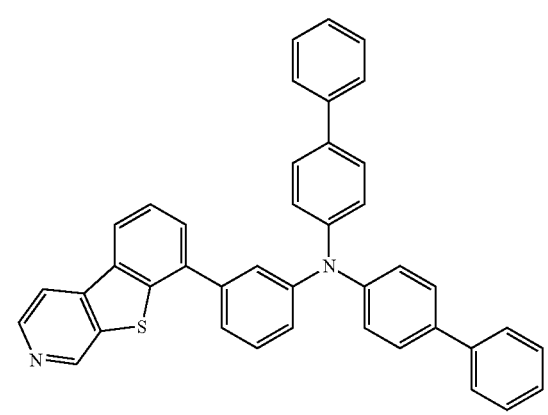
21
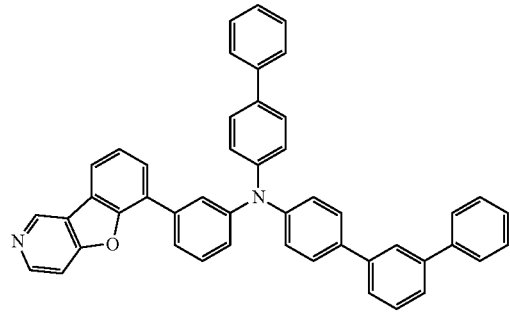
22
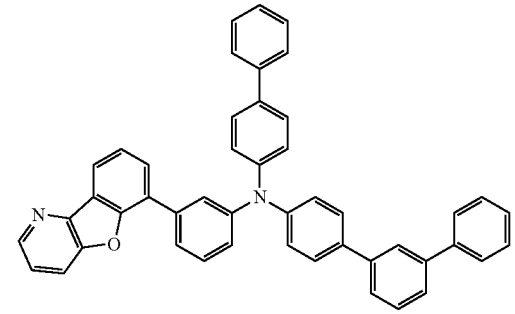
23
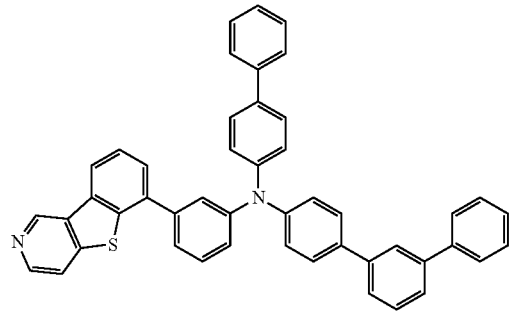
24
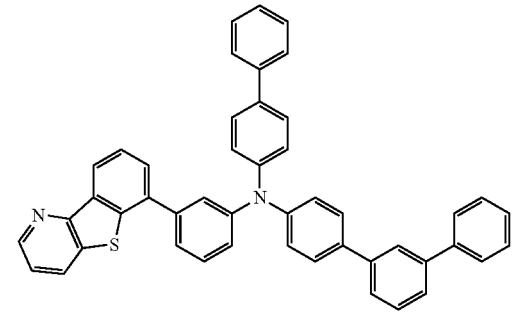

-continued
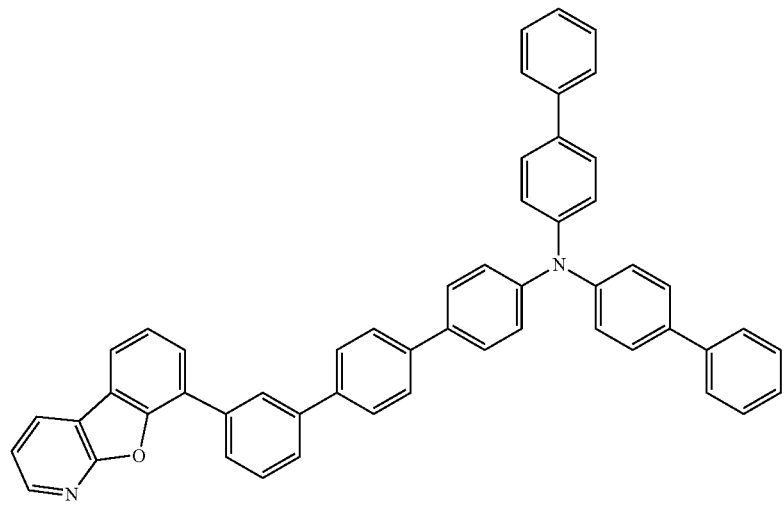
25
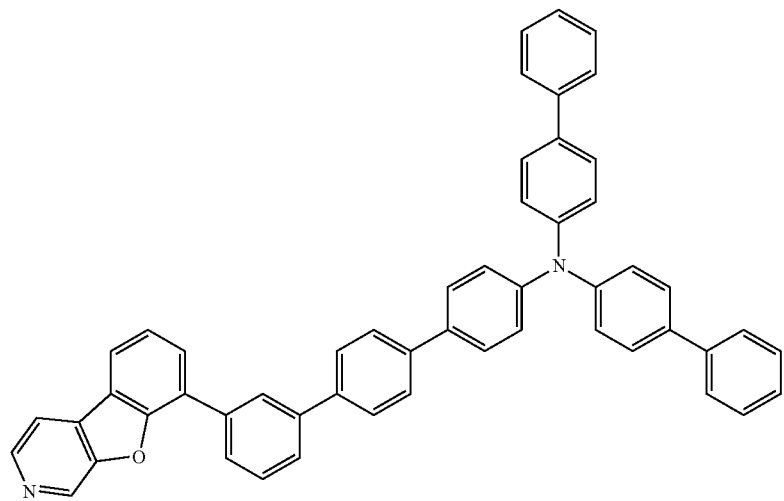
26
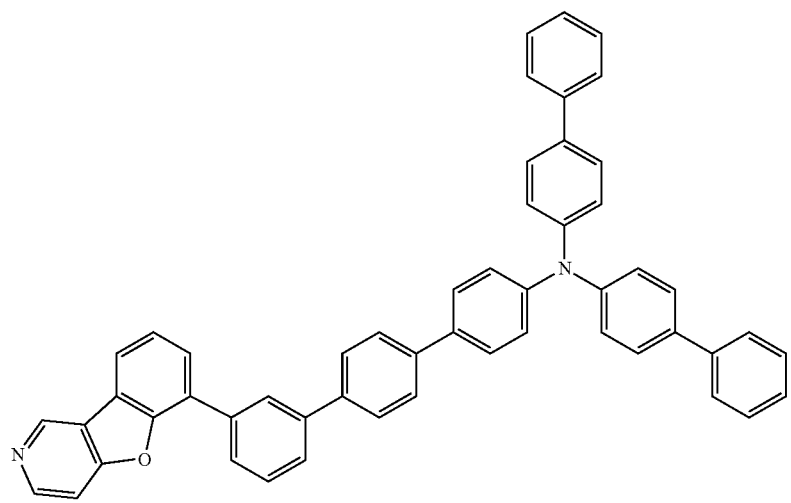
27

-continued
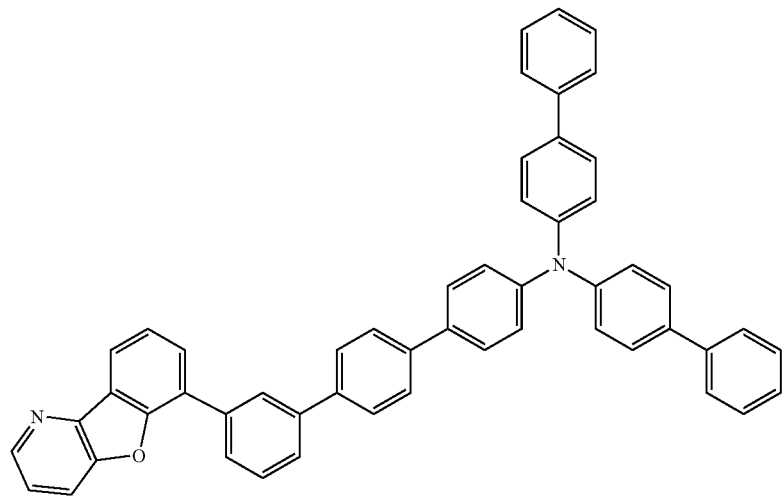
28
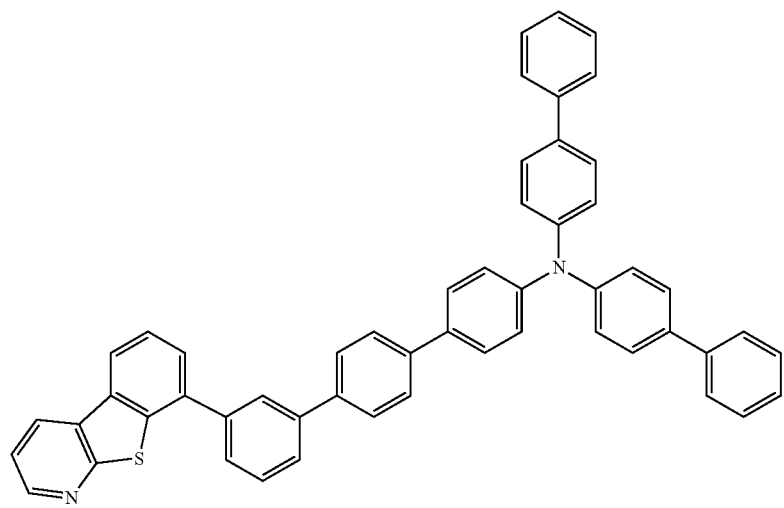
29
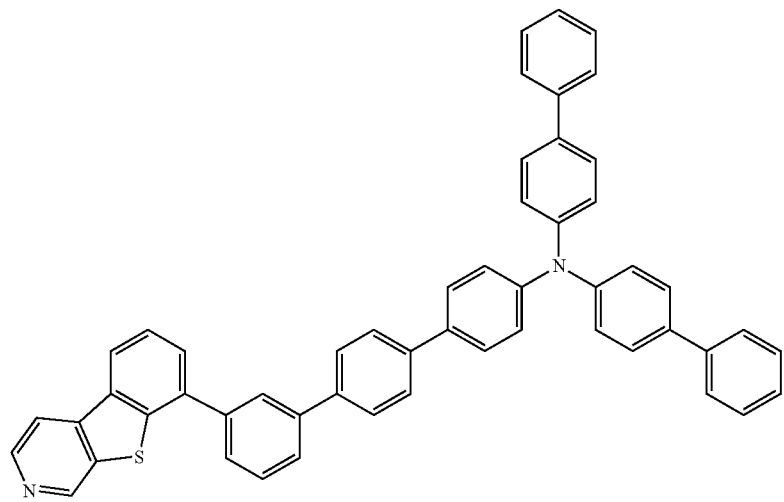
30

-continued
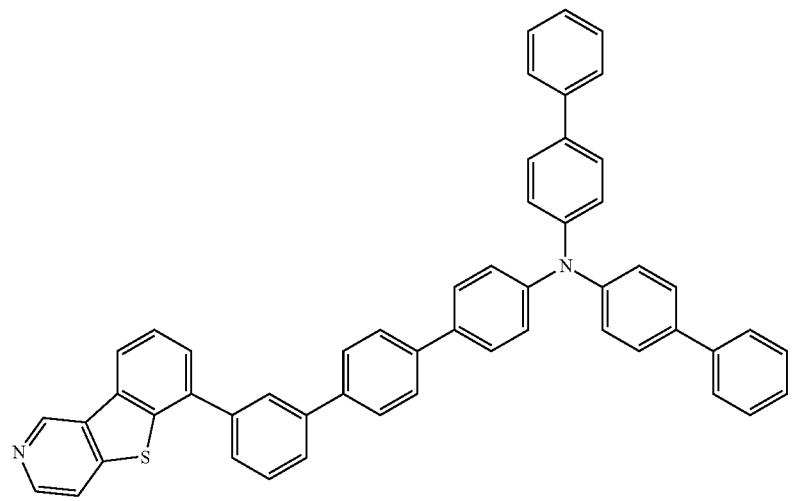
31
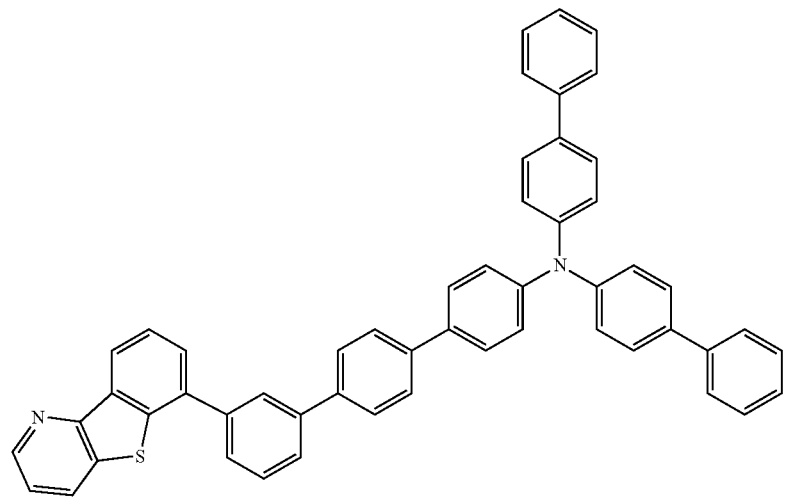
32
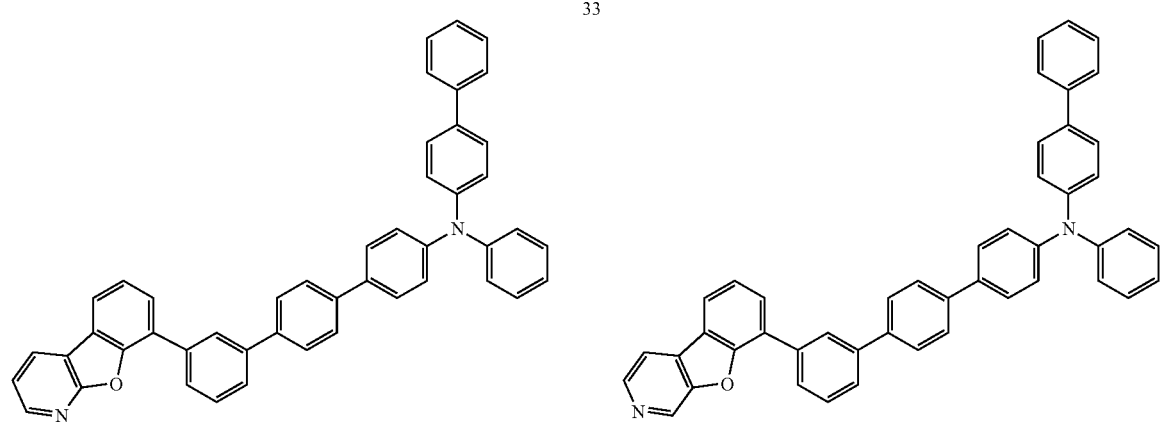
33  34

-continued
35
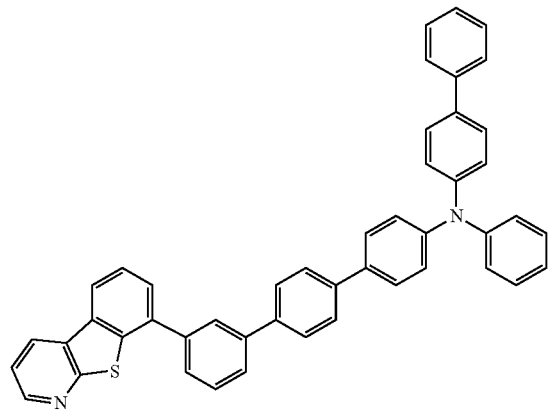
36
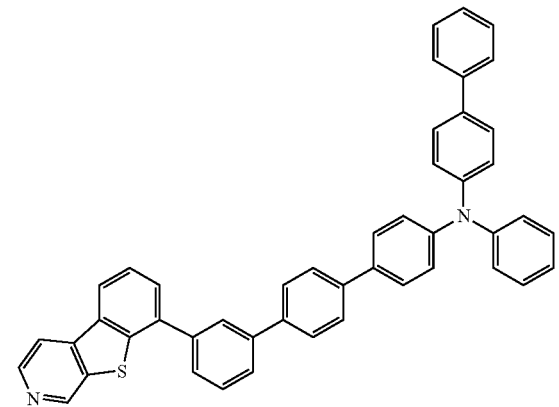
37
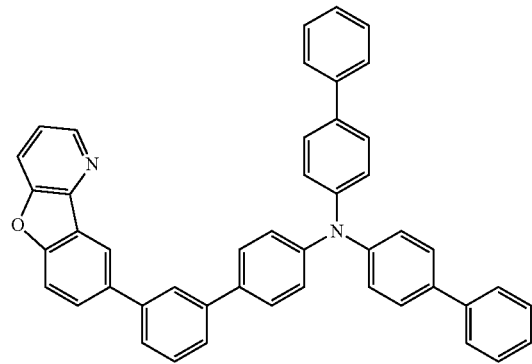
38
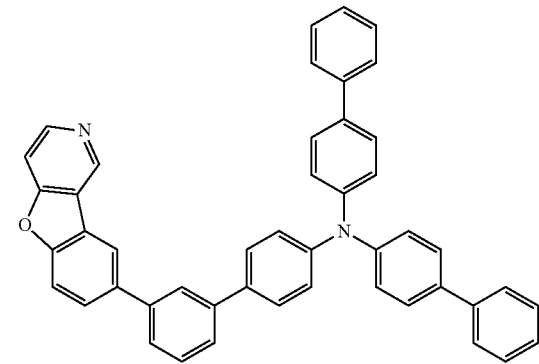
39
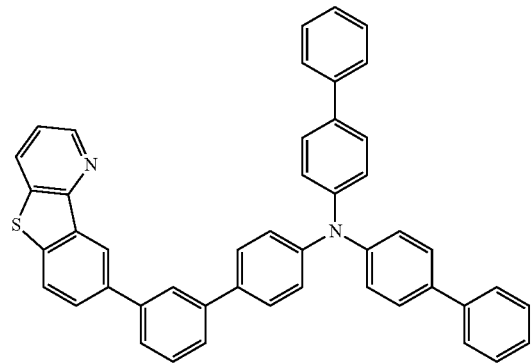
40
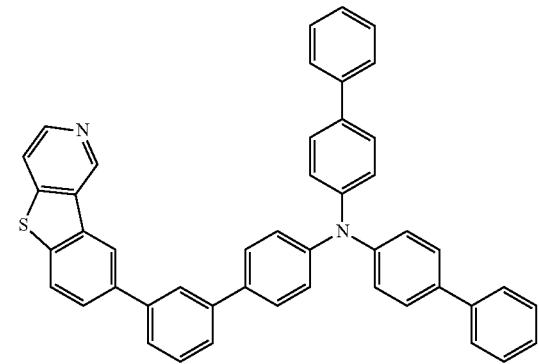
41
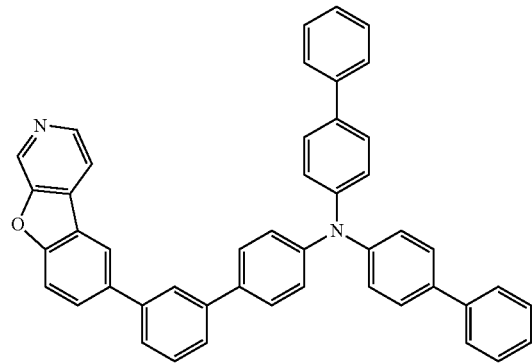
42
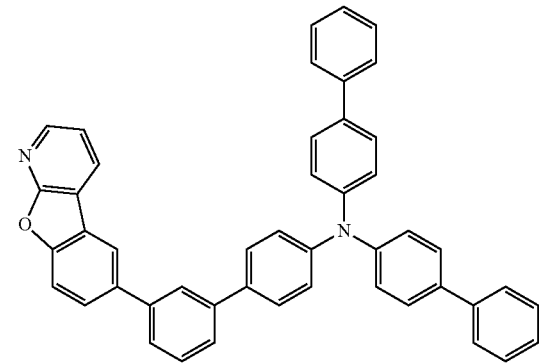

-continued
43
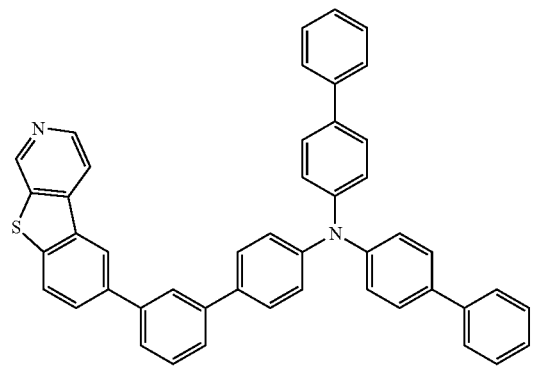
44
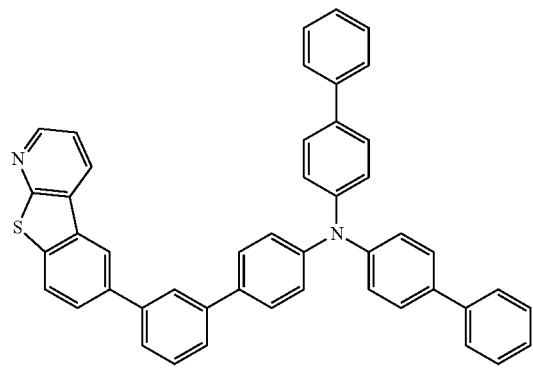
45
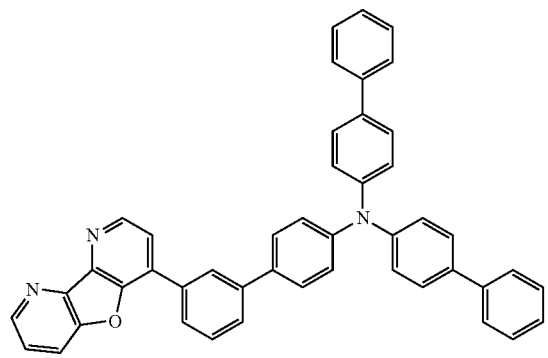
46
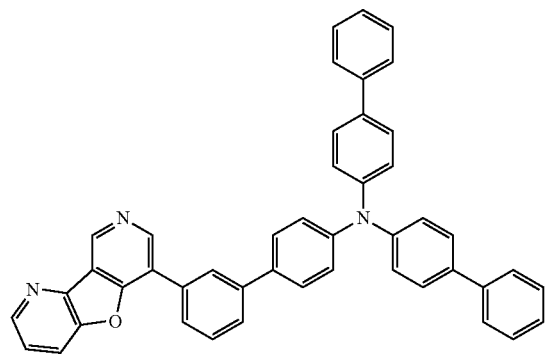
47
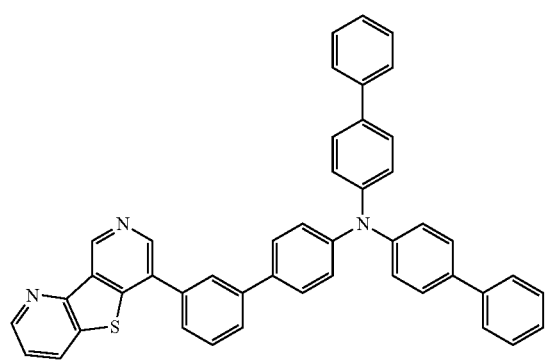
48
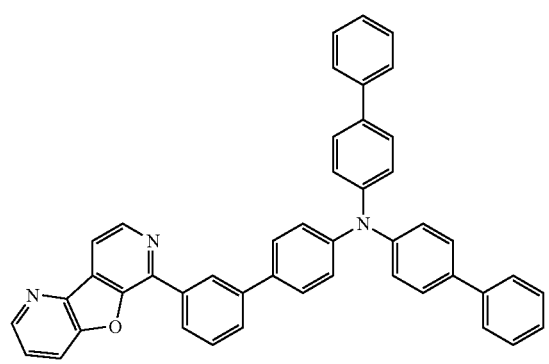
49
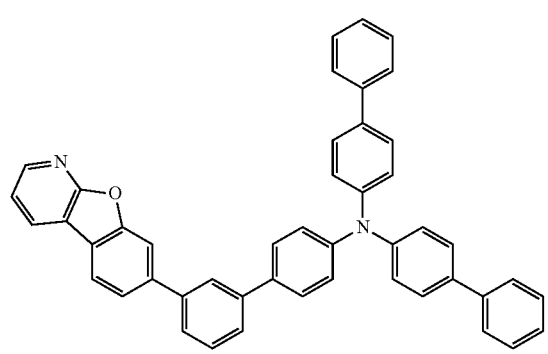
50
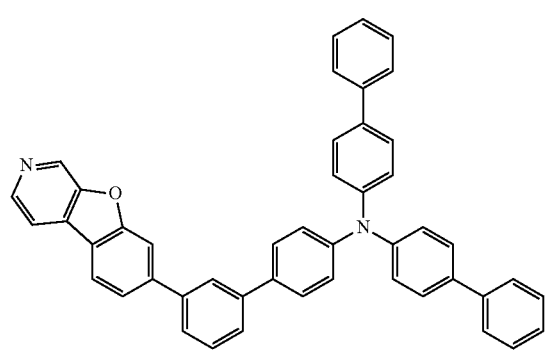

-continued
51
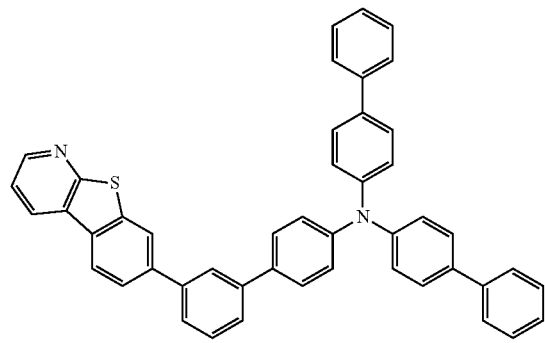
52
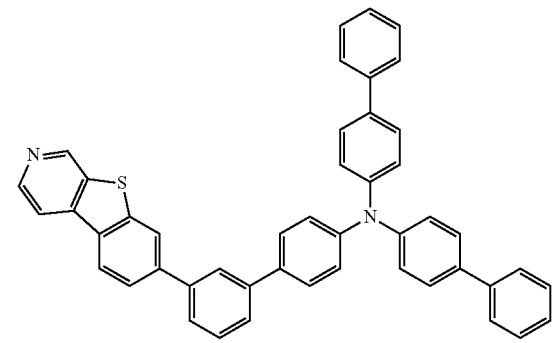
53
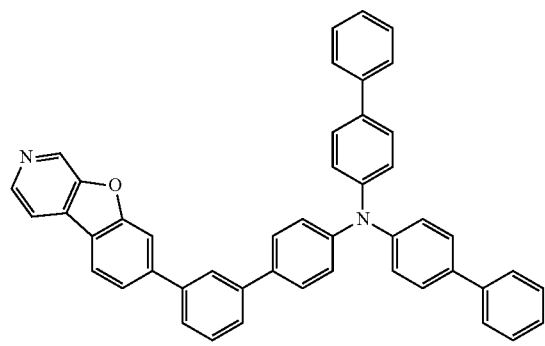
54
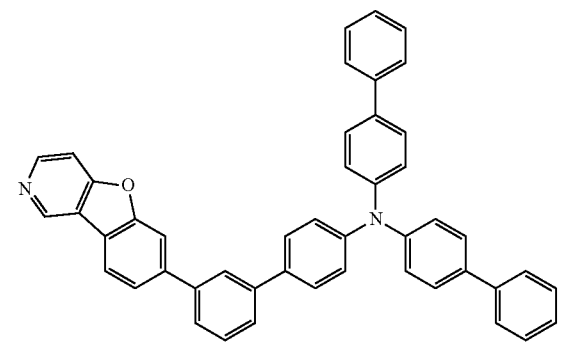
55
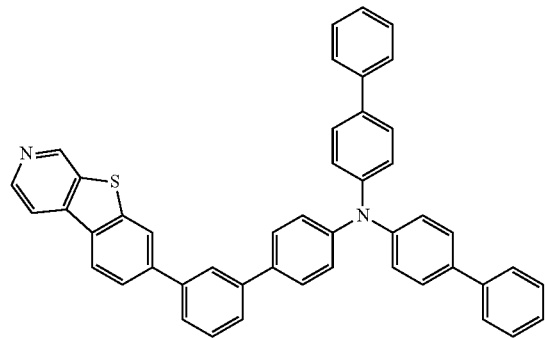
56
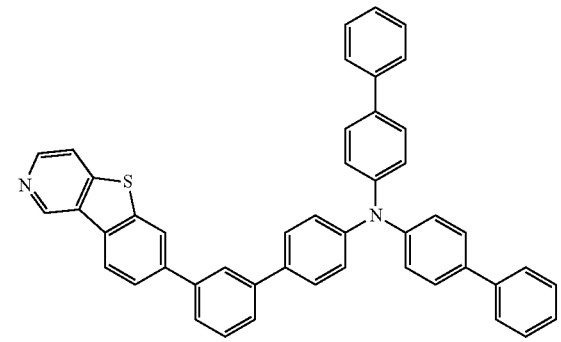
57
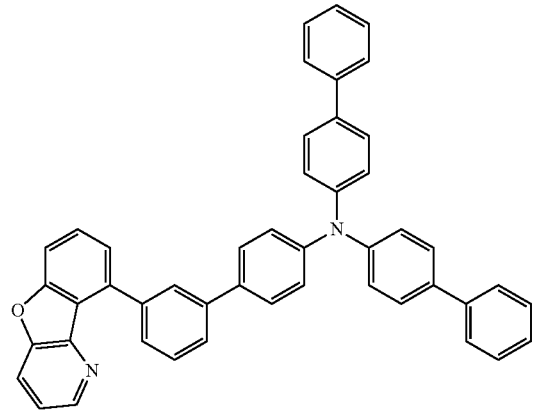
58
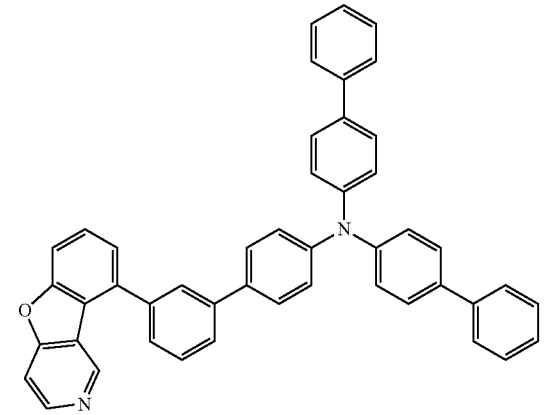

-continued
59
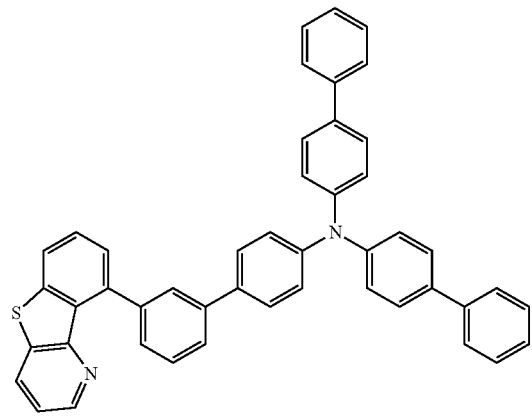
60
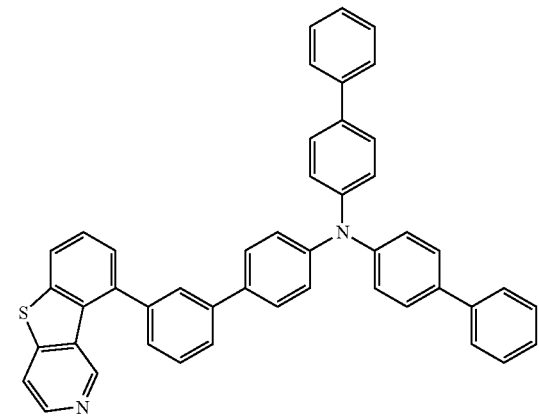
61
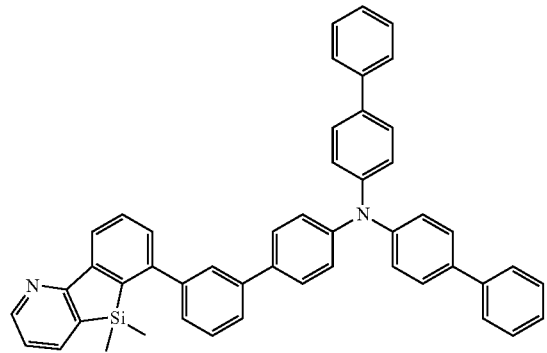
62
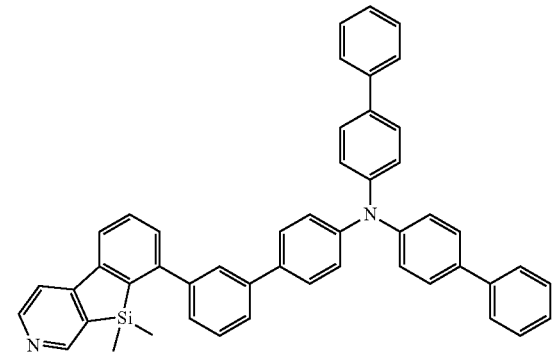
63
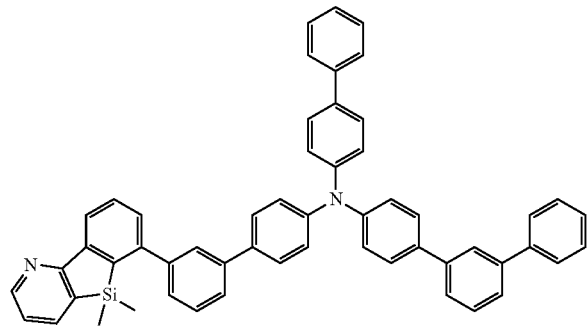
64
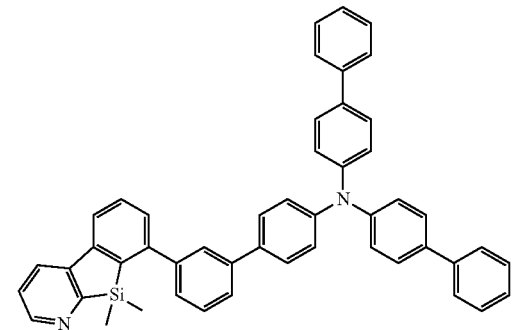
65
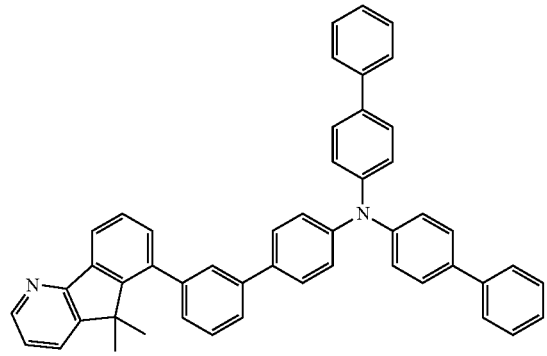
66
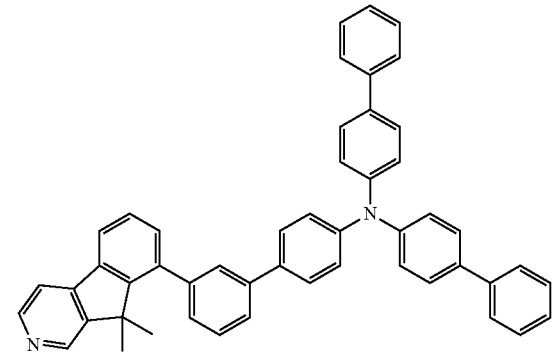

67
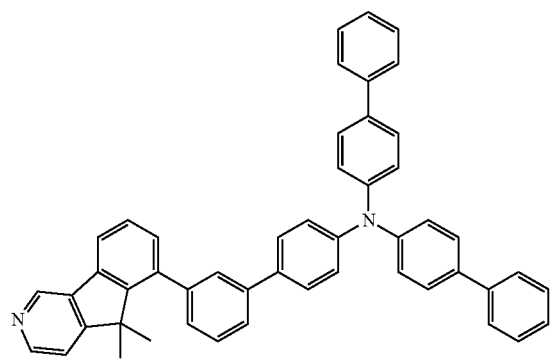
68
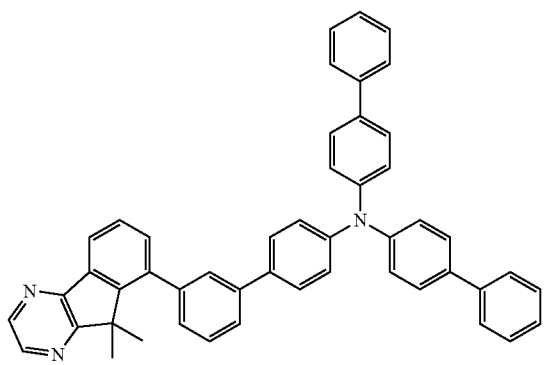
69
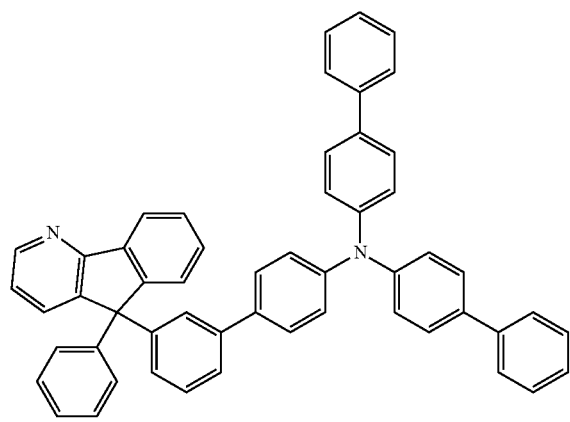
70
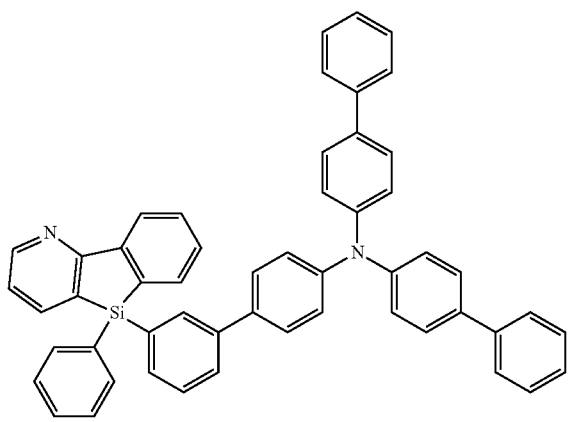
71
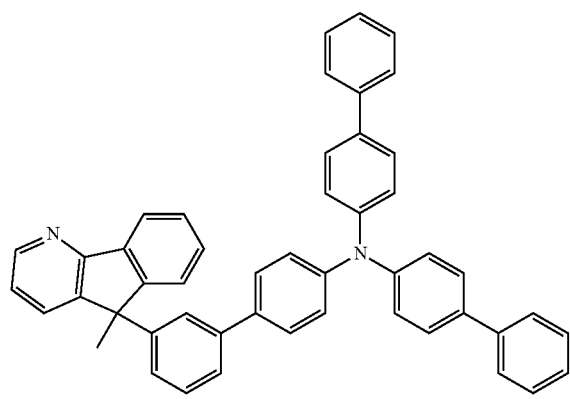
72
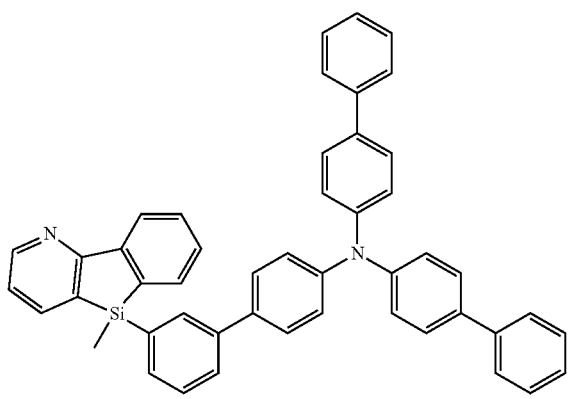
73
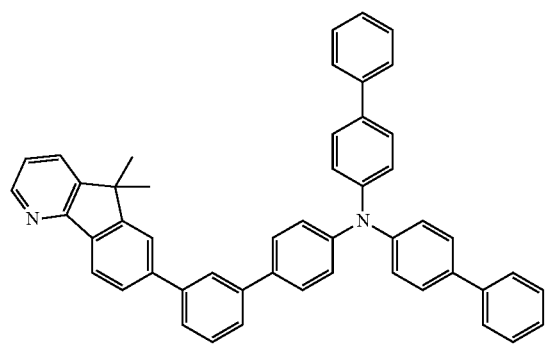
74
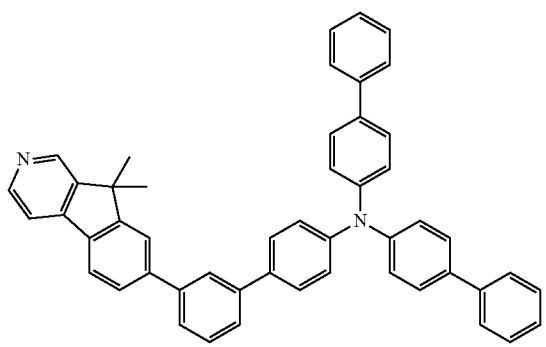

-continued
75
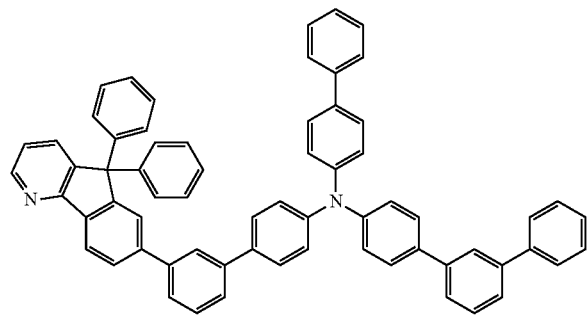
76
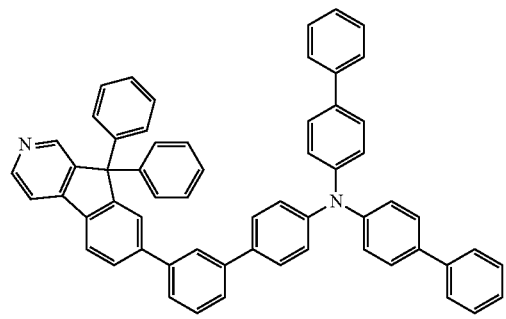
77
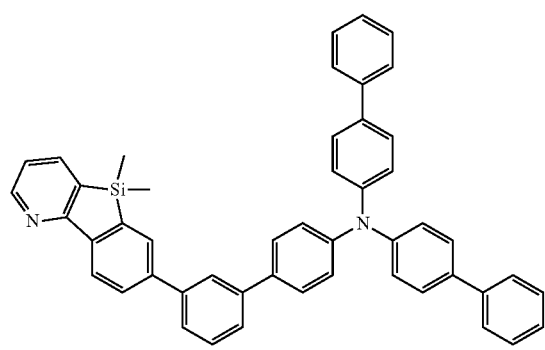
78
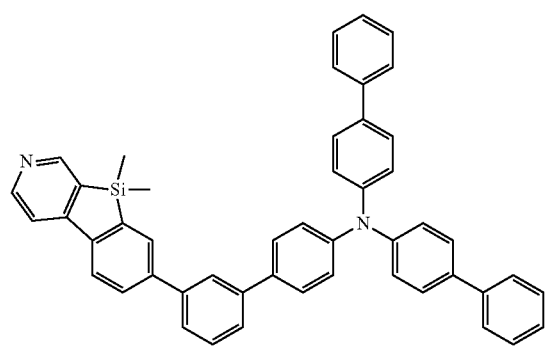
79
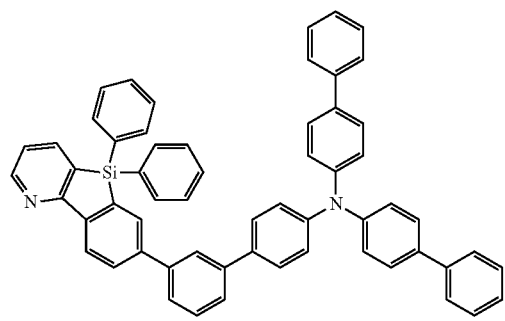
80
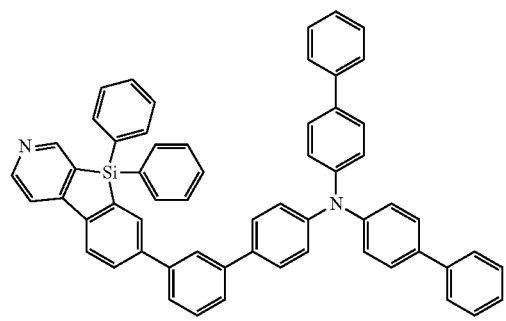
81
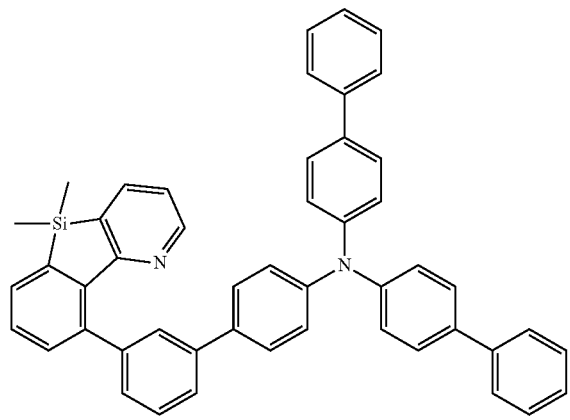
82
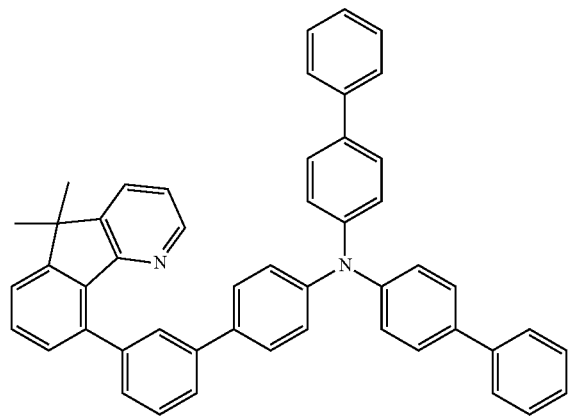

-continued

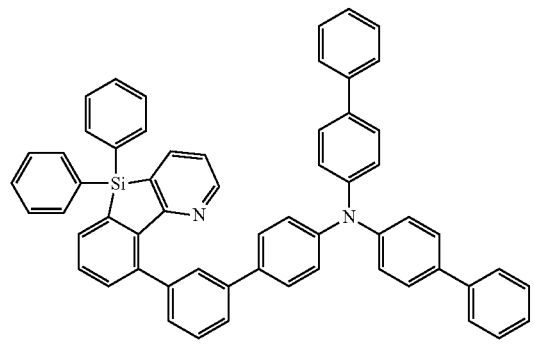
83

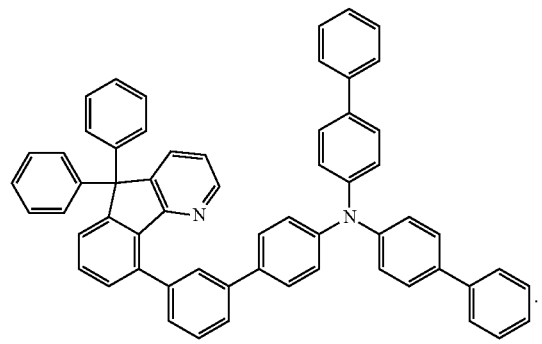
84

3. An organic electroluminescent (EL) device comprising a material of claim 1, wherein the material is included in at least one layer of stacking layers between an emission layer and an anode.

4. An organic electroluminescent (EL) device comprising a material of claim 2, wherein the material is included in at least one layer of stacking layers between an emission layer and an anode.

* * * * *